(12) United States Patent
Han et al.

(10) Patent No.: US 11,739,124 B2
(45) Date of Patent: Aug. 29, 2023

(54) ACETYL-COA CARBOSYLASE2 ANTISENSE OLIGONUCLEOTIDES

(71) Applicant: OLIPASS CORPORATION, Gyeonggi-do (KR)

(72) Inventors: Seon-Young Han, Gangwon-do (KR); Kiho Sung, Gyeonggi-do (KR); Myunghyo Hong, Gyeonggi-do (KR); Dayoung Kang, Seoul (KR); Jeong-Seok Heo, Gyeonggi-do (KR); Kang Won Jang, Gyeonggi-do (KR)

(73) Assignee: OLIPASS CORPORATION, Gyeonggi-Do (KR)

( * ) Notice: Subject to any disclaimer, the term of this patent is extended or adjusted under 35 U.S.C. 154(b) by 233 days.

(21) Appl. No.: 17/266,763

(22) PCT Filed: Aug. 5, 2019

(86) PCT No.: PCT/KR2019/009697
§ 371 (c)(1),
(2) Date: Feb. 8, 2021

(87) PCT Pub. No.: WO2020/036353
PCT Pub. Date: Feb. 20, 2020

(65) Prior Publication Data
US 2021/0363190 A1 Nov. 25, 2021

(30) Foreign Application Priority Data
Aug. 14, 2018 (KR) .................. 10-2018-0095124

(51) Int. Cl.
| A61K 38/00 | (2006.01) |
| C07K 14/00 | (2006.01) |
| A61K 8/64 | (2006.01) |
| A61Q 19/08 | (2006.01) |

(52) U.S. Cl.
CPC ............ *C07K 14/003* (2013.01); *A61K 8/64* (2013.01); *A61Q 19/08* (2013.01); *A61K 38/00* (2013.01)

(58) Field of Classification Search
None
See application file for complete search history.

(56) References Cited

U.S. PATENT DOCUMENTS

| 6,133,444 | A | 10/2000 | Coull et al. |
| 6,617,422 | B1 | 9/2003 | Nielsen et al. |
| 2003/0105044 | A1 | 6/2003 | Baker et al. |
| 2004/0215006 | A1 | 10/2004 | Bennett et al. |
| 2014/0314697 | A1 | 10/2014 | Wang et al. |
| 2015/0274782 | A1 | 10/2015 | Cai et al. |
| 2017/0340544 | A1 | 11/2017 | Chung et al. |
| 2021/0292369 | A1 | 9/2021 | Han et al. |
| 2021/0363190 | A1 | 11/2021 | Han et al. |
| 2022/0363720 | A1 | 11/2022 | Han et al. |

FOREIGN PATENT DOCUMENTS

| KR | 20120073536 A | 7/2012 |
| RU | 2011125776 A | 2/2013 |
| WO | 9640685 A1 | 12/1996 |
| WO | 2006110775 A2 | 10/2006 |
| WO | 2009113828 A2 | 9/2009 |
| WO | 2010123983 A1 | 10/2010 |
| WO | 2013112548 A1 | 8/2013 |
| WO | 2018029517 A1 | 2/2018 |
| WO | 2018051175 A1 | 3/2018 |
| WO | 2018069764 A1 | 4/2018 |
| WO | 2018122610 A1 | 7/2018 |
| WO | 2018127733 A1 | 7/2018 |
| WO | 2018138585 A1 | 8/2018 |
| WO | 2019022434 A1 | 1/2019 |
| WO | 2019221570 A1 | 11/2019 |
| WO | 2020036353 A1 | 2/2020 |
| WO | 2021010723 A1 | 1/2021 |

OTHER PUBLICATIONS

International Search Report and Written Opinion for International Application No. PCT/KR2018/008143 (dated Oct. 31, 2018).
Siwkowski et al., "Identification and Functional Validation of PNAs that Inhibit Murine CD40 Expression by Redirection of Splicing," Nucleic Acids Reseach 32(9):2695-2706 (2004).
Boissy et al., "DeoxyArbutin: A Novel Reversible Tyrosinase Inhibitor with Effective In Vivo Skin Lightening Potency," Experimental Dermatology 14:601-608 (2005).
Ebanks et al., "Mechanisms Regulating Skin Pigmentation: The Rise and Fall of Complexion Coloration," Int. J. Mol. Sci. 10:4066-4087 (2009).
Gillbro et al., "The Melanogenesis and Mechanisms of Skin-Lightening Agents—Existing and New Approaches," International Journal of Cosmetic Science 33:210-221 (2011).
Chang, T., "An Updated Review of Tyrosinase Inhibitors," Int. J. Mol. Sci. 10:2440-2475 (2009).
Arndt et al., "Topical Use of Hydroquinone as a Depigmenting Agent," JAMA 94(9):117-119 (1965).
Maeda et al., "Arbutin: Mechanism of Its Depigmenting Action in Human Melanocyte Culture," The Journal of Phamacology and Experimental Therapeutics 276(2):765-769 (1996).
Hu et al., "Effects of Hydroquinone and its Glucoside Derivatives on Melanogenesis and Antioxidation: Biosafety as Skin Whitening Agents," Journal of Dermatological Science 55:179-184 (2009).

(Continued)

*Primary Examiner* — Aradhana Sasan
*Assistant Examiner* — Mercy H Sabila
(74) *Attorney, Agent, or Firm* — Heslin Rothenberg Farley & Mesiti P.C.

(57) ABSTRACT

The present invention provides the peptide nucleic acid derivative which targets 5' splice site of the human ACC2 pre-mRNA "exon 12". The peptide nucleic acid derivatives in the present invention strongly induce splice variants of the human ACC2 mRNA in cell and are very useful to treat conditions or disorders of skin aging associated with the human ACC2 protein.

5 Claims, 21 Drawing Sheets
Specification includes a Sequence Listing.

(56) References Cited

OTHER PUBLICATIONS

Cabanes et al., "Kojic Acid, a Cosmetic Skin Whitening Agent, is a Slow-Binding Inhibitor of Catecholase Activity of Tyrosinase," J. Pharm. Pharmacol. 46:982-985 (1994).
Badreshia-Bansal et al., "Insight into Skin Lightening Cosmeceuticals for Women of Color," Journal of Drugs in Dermatology 6(1):32-39 (2007).
Pillaiyar et al., "Skin Whitening Agents: Medicinal Chemistry Perspective of Tyrosinase Inhibitors," Journal of Enzyme Inhibition and Medicinal Chemistry 32(1):403-425 (2017).
Black, D., "Mechanisms of Alternative Pre-Messenger RNA Splicing," Annu. Rev. Biochem. (72):291-336 (2003).
Matlin et al., "Understanding Alternative Splicing: Towards A Cellular Code," Nature Reviews, Molecular Cell Biology 6:386-398 (2005).
Matera et al., "A Day in the Life of the Spliceosome," Nat. Rev. Mol. Cell Biol. 15(2):108-121 (2014).
Braasch et al., "Novel Antisense and Peptide Nucleic Acid Strategies for Controlling Gene Expression," Biochemistry 41(14):4503-4510 (2002).
Stein et al., "Oligodeoxynucleotides as Inhibitors of Gene Expression: A Review," Cancer Research 48:2659-2668 (1988).
Chan et al., "Antisense Oligonucleotides: From Design To Therapeutic Application," Clinical and Experimental Pharmacology and Physiology 33:533-540 (2006).
Eckstein, F., "Nucleoside Phosphorothioates," Ann. Rev. Biochem. 54:367-402 (1985).
Bijsterbosch et al., "In Vivo Fate of Phosphorothioate Antisense Oligodeoxynucleotides: Predominant Uptake by Scavenger Receptors on Endothelial Liver Cells," Nucleic Acids Research 25(16):3290-3296 (1997).
Merki et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," American Heart Association Journals Circulation, pp. 743-753 (2008).
Liu, G., "Technology Evaluation: ISIS-113715, Isis," Current Opinion in Molecular Therapeutics 6(3):331-336 (2004).
Kaur et al., "Thermodynamic, Counterion, and Hydration Effects for the Incorporation of Locked Nucleic Acid Nucleotides into DNA Duplexes," Biochemistry 45:7347-7355 (2006).
Karkare et al., "Promising Nucleic Acid Analogs and Mimics: Characteristic Features and Applications of PNA, LNA, and Morpholino," Appl. Microbiol. Biotechnol. 71:575-586 (2006).
Nielsen et al., "Sequence-Selective Recognition of DNA by Strand Displacement with a Thymine-Substituted Polyamide," Science, New Series 254(5037):1497-1500 (1991).
Egholm et al., "PNA Hybridizes to Complementary Oligonucleotides Obeying the Watson-Crick Hydrogen-Bonding Rules," Nature 365:566-568 (1993).
Koppelhus et al., "Cellular Delivery of Peptide Nucleic Acid (PNA)," Advanced Drug Delivery Reviews 55:267-280 (2003).
Agrawal et al., "RNA Interference: Biology, Mechanism, and Applications," Microbiology and Molecular Biology Reviews 67(4):657-685 (2003).
An et al., "Inhibition of Melanogenesis by Tyrosinase siRNA in Human Melanocytes," BMB Reports 42(3):178-183 (2009).
Xiu-Hua et al., "Tyrosinase Small Interfering RNA Effectively Suppresses Tyrosinase Gene Expression In Vitro and In Vivo," Molecular Biology International, Article ID 240472: 1-6 (2010).
International Search Report and Written Opinion for International Application No. PCT/KR2019/005994 (dated Aug. 20, 2019).
International Search Report and Written Opinion for International Application No. PCT/KR2019/009697 (dated Nov. 29, 2019).
Yucesoy et al., "Genetic Basis of Irritant Susceptibility in Health Care Workers", J Occup Environ Med., vol. 58(8), pp. 753-759. Aug. 2016.
Knäuper et al. "The Role of Exon 5 in Fibroblast Collagenase (MMP-1) Substrate Specificity and Inhibitor Selectivity", Eur. J. Biochem., vol. 268, pp. 1888-196. 2001.
International Search Report and Written Opinion for International Application No. PCT/KR2020/009228 (dated Nov. 6, 2020).
Desai, S., "Hyperpigmentation Therapy: A Review," The Journal of Clinical and Aesthetic Dermatology 7(8):13-17 (2014).

Fig. 2b
Examples of Non-substituted Alkylacyl Radical
Examples of Substituted Alkylacyl Radical
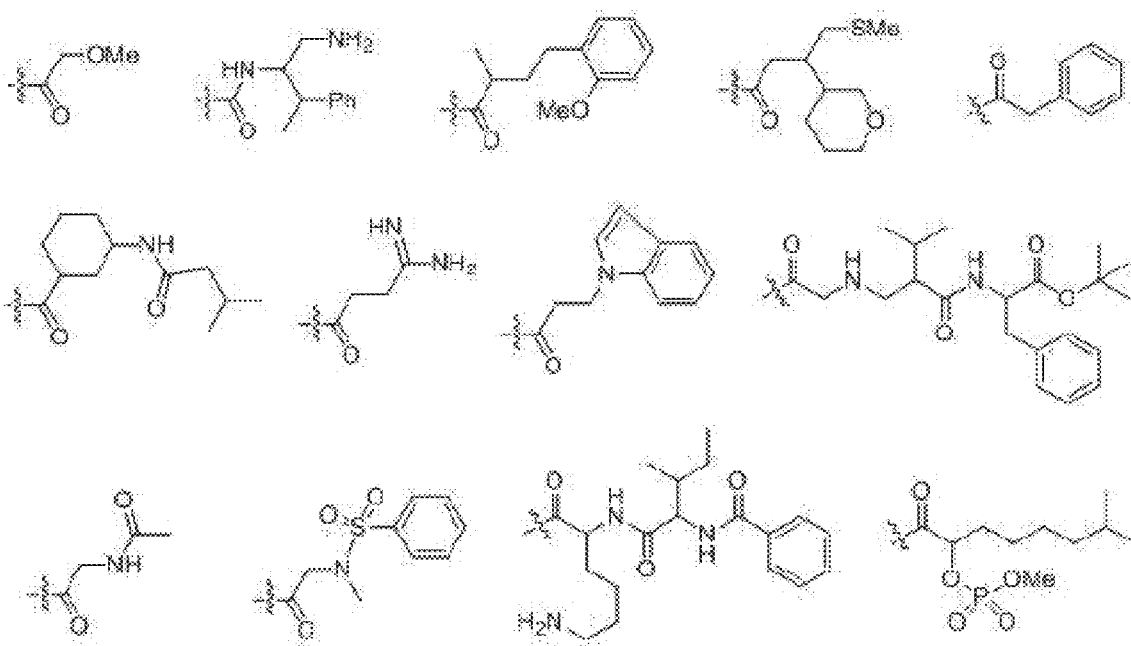
Examples of Substituted or Non-substituted Arylacyl Radical
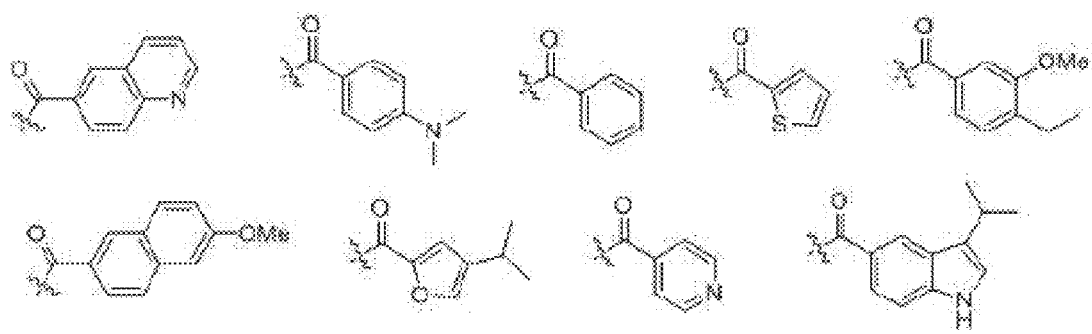

Fig. 2c
Examples of Substituted Alkylamino or Arylamino Radical
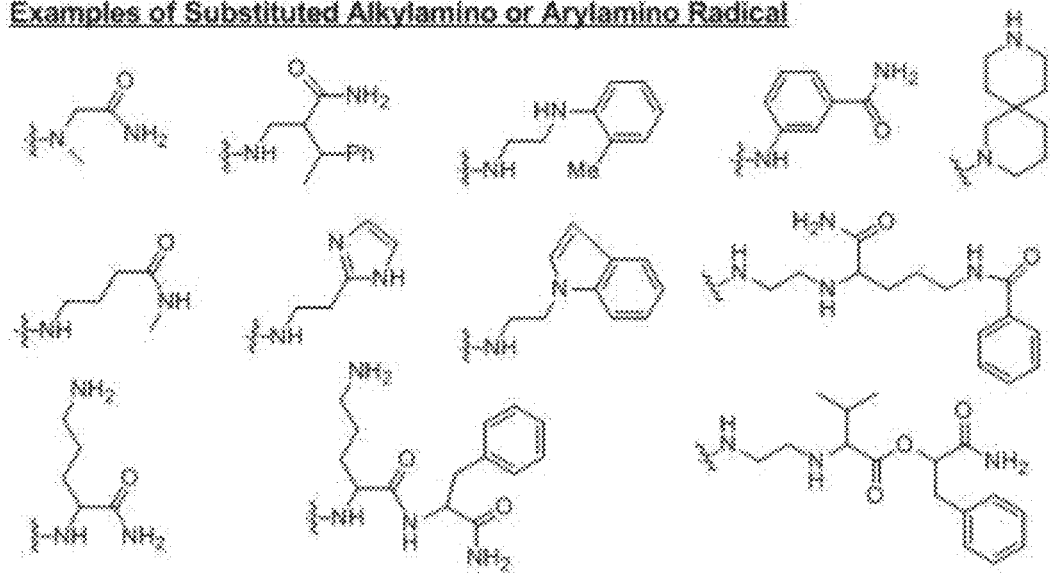
Examples of Substituted or Non-substituted Aryl Radical
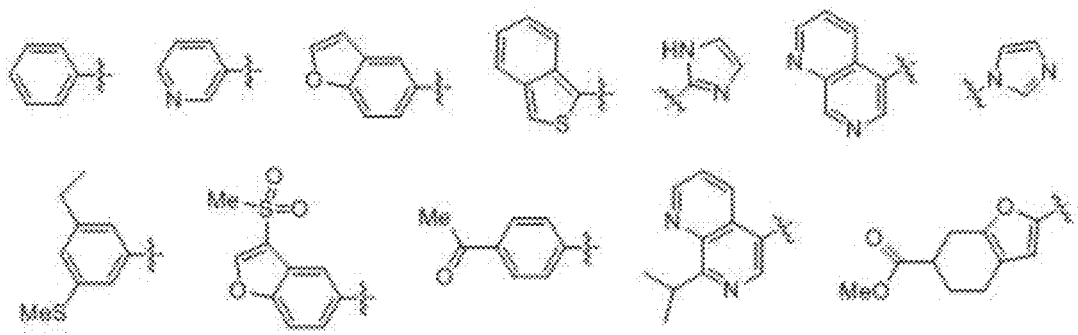
Examples of Substituted or Non-substituted Alkylsulfonyl or Arylsulfonyl Radical
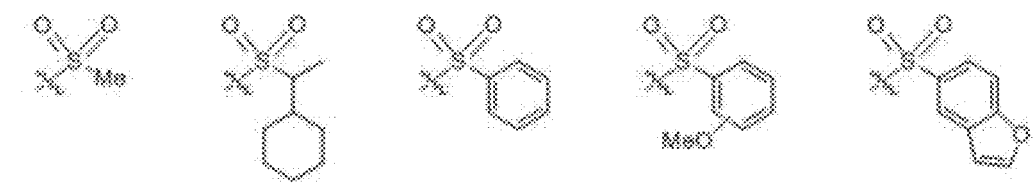
Examples of Substituted or Non-substituted Alkyl- or Aryl-phosphonyl Radical
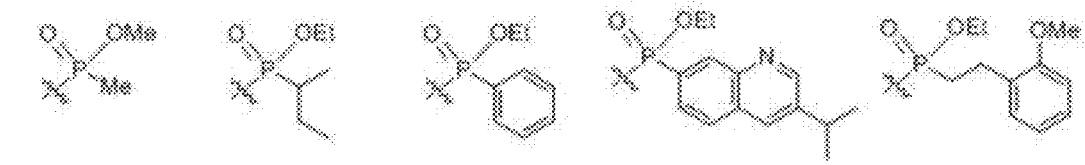

Fig. 2d
Examples of Substituted or Non-substituted Alkyloxycarbonyl Radical
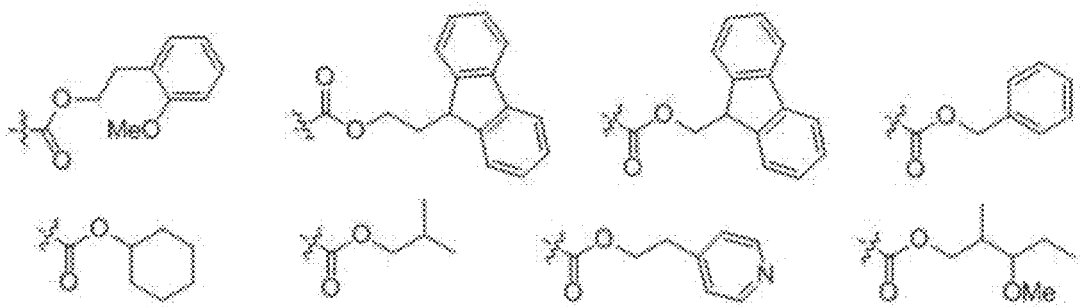
Examples of Substituted or Non-substituted Aryloxycarbonyl Radical
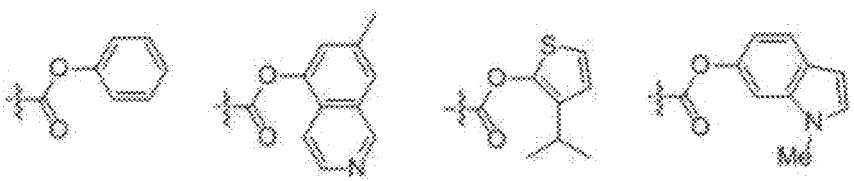
Examples of Substituted or Non-substituted Alkylaminocarbonyl Radical
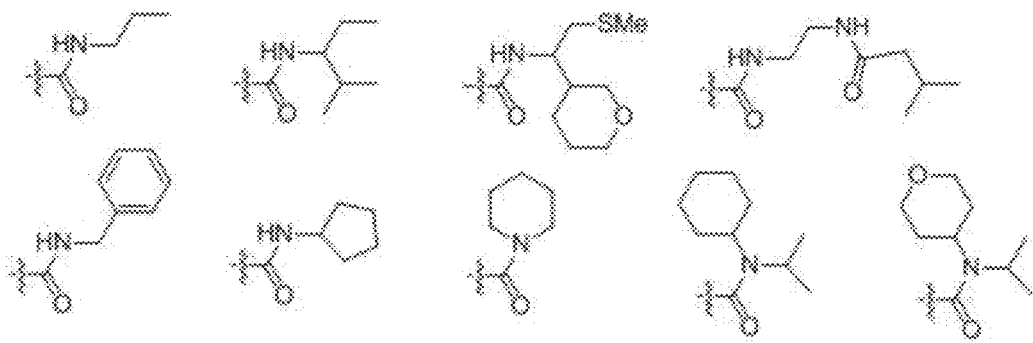
Examples of Substituted or Non-substituted Arylaminocarbonyl Radical
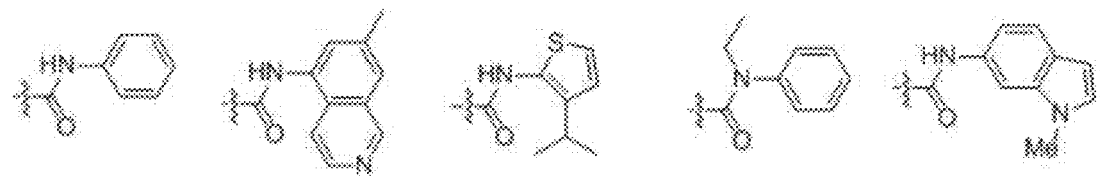

Fig. 2e
Examples of Substituted or Non-substituted Alkyloxythiocarbonyl Radical
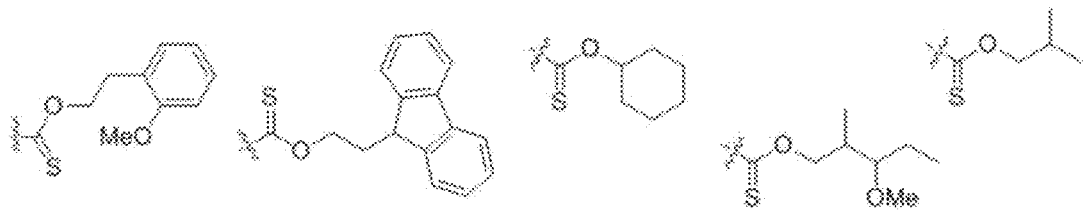
Examples of Substituted or Non-substituted Alkylaminothiocarbonyl Radical
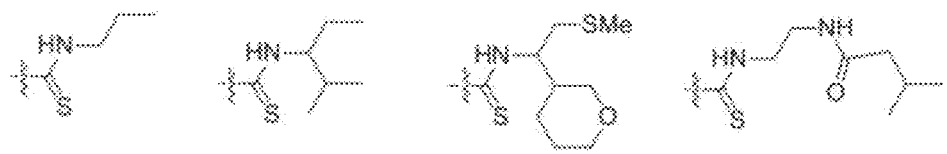
Examples of Substituted or Non-substituted Arylaminothiocarbonyl Radical
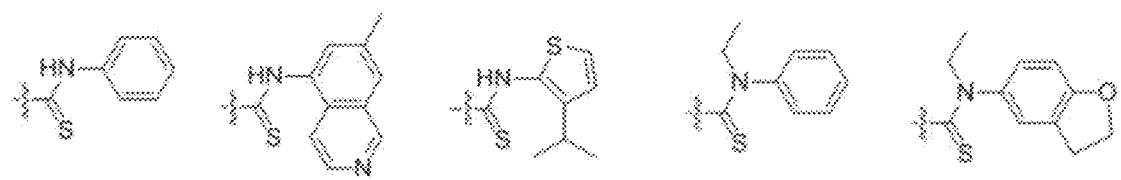
Examples of Substituted or Non-substituted Aryloxythiocarbonyl Radical
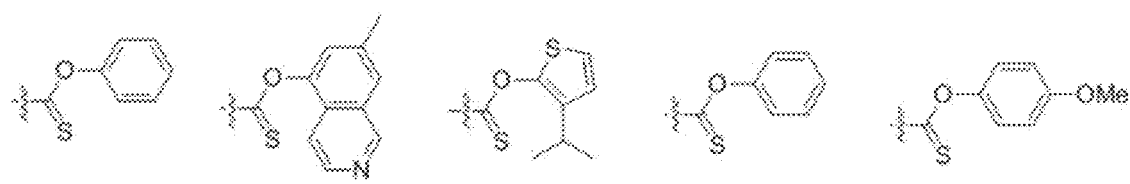

Fig. 3
PNA Monomer
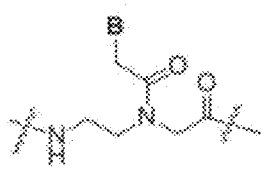
B : Nucleobase
X : O (oxygen atom)
m : Integer
n : Integer
Adenine
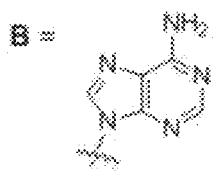
Guanine
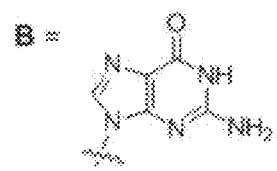
Thymine
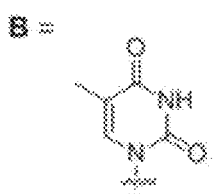
Cytosine
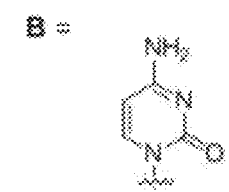
Modified Cytosine
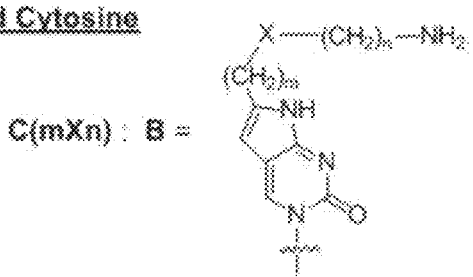
C(mXn) : B =
Modified Adenine
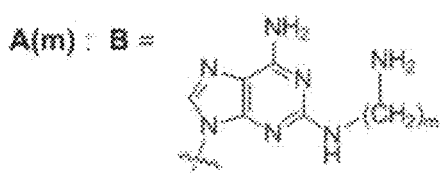
A(m) : B =
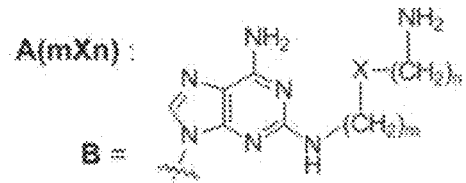
A(mXn) : B =
Modified Guanine
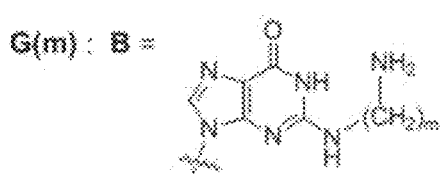
G(m) : B =
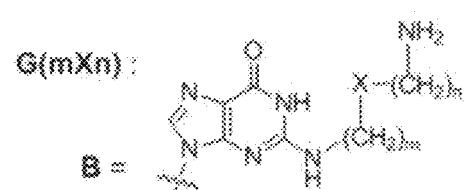
G(mXn) : B =

Fig. 5
Fmoc-PNA Monomer
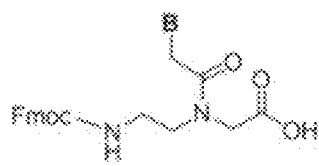
B : Nucleobase with protecting group(s)
X : methylene, oxygen, sulfur, or Boc-protected amino
m : Integer
n : Integer
Boc- 
Modified Cytosine
C(mXn) : B = 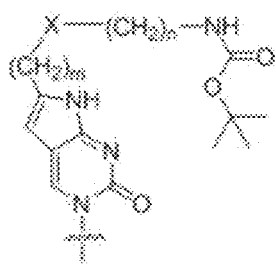
Modified Adenine
A(mXn) :
B = 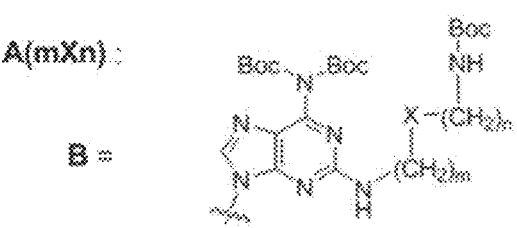
Modified Guanine
G(mXn) :
B = 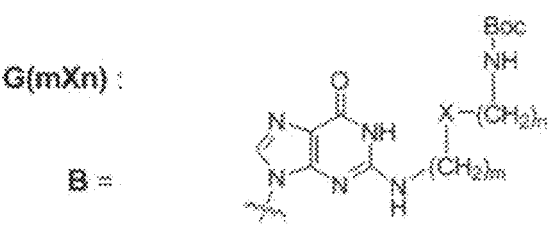

```
                    SEQUENCE LISTING

<160> NUMBER OF SEQ ID NOS: 13

<210> SEQ ID NO 1
<211> LENGTH: 14
<212> TYPE: DNA
<213> ORGANISM: Artificial
<220> FEATURE:
<223> OTHER INFORMATION: PNA modified oligonucleotide
<220> FEATURE:
<221> NAME/KEY: misc_feature
<222> LOCATION: (1)..(14)
<223> OTHER INFORMATION: PNA modified oligonucleotide, human acetyl-CoA
      carboxylase2 targeted artificial sequence
<220> FEATURE:
<221> NAME/KEY: misc_feature
<222> LOCATION: (1)..(1)
<223> OTHER INFORMATION: Carbamated N-terminal
<220> FEATURE:
<221> NAME/KEY: modified_base
<222> LOCATION: (3)..(3)
<223> OTHER INFORMATION: n is a, g, c, or t
<220> FEATURE:
<221> NAME/KEY: modified_base
<222> LOCATION: (6)..(6)
<223> OTHER INFORMATION: n is a, g, c, or t
<220> FEATURE:
<221> NAME/KEY: modified_base
<222> LOCATION: (8)..(8)
<223> OTHER INFORMATION: n is a, g, c, or t
<220> FEATURE:
<221> NAME/KEY: modified_base
<222> LOCATION: (11)..(11)
<223> OTHER INFORMATION: n is a, g, c, or t
<220> FEATURE:
<221> NAME/KEY: modified_base
<222> LOCATION: (13)..(13)
<223> OTHER INFORMATION: n is a, g, c, or t

<400> SEQUENCE: 1
ctnacnanat ngnc                                                    14
```

```
<210> SEQ ID NO 2
<211> LENGTH: 16
<212> TYPE: DNA
<213> ORGANISM: Artificial
<220> FEATURE:
<223> OTHER INFORMATION: PNA modified oligonucleotide
<220> FEATURE:
<221> NAME/KEY: misc_feature
<222> LOCATION: (1)..(16)
<223> OTHER INFORMATION: PNA modified oligonucleotide, human acetyl-CoA
      carboxylase2 targeted artificial sequence
<220> FEATURE:
<221> NAME/KEY: misc_feature
<222> LOCATION: (1)..(1)
<223> OTHER INFORMATION: Carbamated N-terminal
<220> FEATURE:
<221> NAME/KEY: modified_base
<222> LOCATION: (2)..(3)
<223> OTHER INFORMATION: n is a, g, c, or t
<220> FEATURE:
<221> NAME/KEY: modified_base
<222> LOCATION: (6)..(6)
<223> OTHER INFORMATION: n is a, g, c, or t
<220> FEATURE:
<221> NAME/KEY: modified_base
<222> LOCATION: (9)..(9)
<223> OTHER INFORMATION: n is a, g, c, or t
<220> FEATURE:
<221> NAME/KEY: modified_base
<222> LOCATION: (11)..(11)
<223> OTHER INFORMATION: n is a, g, c, or t
<220> FEATURE:
<221> NAME/KEY: modified_base
<222> LOCATION: (13)..(13)
<223> OTHER INFORMATION: n is a, g, c, or t
<220> FEATURE:
<221> NAME/KEY: modified_base
<222> LOCATION: (15)..(15)
<223> OTHER INFORMATION: n is a, g, c, or t

<400> SEQUENCE: 2
tnntgncgna ntngnc                                                  16

<210> SEQ ID NO 3
<211> LENGTH: 14
<212> TYPE: DNA
<213> ORGANISM: Artificial
<220> FEATURE:
<223> OTHER INFORMATION: PNA modified oligonucleotide
<220> FEATURE:
<221> NAME/KEY: misc_feature
<222> LOCATION: (1)..(14)
<223> OTHER INFORMATION: PNA modified oligonucleotide, human acetyl-CoA
      carboxylase2 targeted artificial sequence
<220> FEATURE:
<221> NAME/KEY: misc_feature
<222> LOCATION: (1)..(1)
<223> OTHER INFORMATION: Carbamated N-terminal
<220> FEATURE:
<221> NAME/KEY: modified_base
<222> LOCATION: (2)..(2)
<223> OTHER INFORMATION: n is a, g, c, or t
<220> FEATURE:
<221> NAME/KEY: modified_base
<222> LOCATION: (5)..(5)
<223> OTHER INFORMATION: n is a, g, c, or t
<220> FEATURE:
<221> NAME/KEY: modified_base
<222> LOCATION: (7)..(7)
<223> OTHER INFORMATION: n is a, g, c, or t
<220> FEATURE:
<221> NAME/KEY: modified_base
<222> LOCATION: (9)..(9)
<223> OTHER INFORMATION: n is a, g, c, or t
<220> FEATURE:
<221> NAME/KEY: modified_base
<222> LOCATION: (11)..(11)
```

<223> OTHER INFORMATION: n is a, g, c, or t
<220> FEATURE:
<221> NAME/KEY: modified_base
<222> LOCATION: (13)..(13)
<223> OTHER INFORMATION: n is a, g, c, or t

<400> SEQUENCE: 3
tnctnangna ntng                                                             14

<210> SEQ ID NO 4
<211> LENGTH: 14
<212> TYPE: DNA
<213> ORGANISM: Artificial
<220> FEATURE:
<223> OTHER INFORMATION: PNA modified oligonucleotide
<220> FEATURE:
<221> NAME/KEY: misc_feature
<222> LOCATION: (1)..(14)
<223> OTHER INFORMATION: PNA modified oligonucleotide, human acetyl-CoA
      carboxylase2 targeted artificial sequence
<220> FEATURE:
<221> NAME/KEY: misc_feature
<222> LOCATION: (1)..(1)
<223> OTHER INFORMATION: Carbamated N-terminal
<220> FEATURE:
<221> NAME/KEY: modified_base
<222> LOCATION: (2)..(2)
<223> OTHER INFORMATION: n is a, g, c, or t
<220> FEATURE:
<221> NAME/KEY: modified_base
<222> LOCATION: (5)..(5)
<223> OTHER INFORMATION: n is a, g, c, or t
<220> FEATURE:
<221> NAME/KEY: modified_base
<222> LOCATION: (8)..(8)
<223> OTHER INFORMATION: n is a, g, c, or t
<220> FEATURE:
<221> NAME/KEY: modified_base
<222> LOCATION: (10)..(10)
<223> OTHER INFORMATION: n is a, g, c, or t
<220> FEATURE:
<221> NAME/KEY: modified_base
<222> LOCATION: (12)..(12)
<223> OTHER INFORMATION: n is a, g, c, or t
<220> FEATURE:
<221> NAME/KEY: modified_base
<222> LOCATION: (14)..(14)
<223> OTHER INFORMATION: n is a, g, c, or t

<400> SEQUENCE: 4
antgncgnan tngn                                                             14

<210> SEQ ID NO 5
<211> LENGTH: 12
<212> TYPE: DNA
<213> ORGANISM: Artificial
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide, human acetyl-CoA
      carboxylase2 targeted artificial sequence
<220> FEATURE:
<221> NAME/KEY: misc_feature
<222> LOCATION: (1)..(1)
<223> OTHER INFORMATION: Carbamated N-terminal
<220> FEATURE:
<221> NAME/KEY: modified_base
<222> LOCATION: (3)..(3)
<223> OTHER INFORMATION: n is a, g, c, or t
<220> FEATURE:
<221> NAME/KEY: modified_base
<222> LOCATION: (5)..(5)
<223> OTHER INFORMATION: n is a, g, c, or t

```
<220> FEATURE:
<221> NAME/KEY: modified_base
<222> LOCATION: (7)..(7)
<223> OTHER INFORMATION: n is a, g, c, or t
<220> FEATURE:
<221> NAME/KEY: modified_base
<222> LOCATION: (9)..(9)
<223> OTHER INFORMATION: n is a, g, c, or t
<220> FEATURE:
<221> NAME/KEY: modified_base
<222> LOCATION: (11)..(11)
<223> OTHER INFORMATION: n is a, g, c, or t

<400> SEQUENCE: 5
ctnangnant ng                                                          12

<210> SEQ ID NO 6
<211> LENGTH: 14
<212> TYPE: DNA
<213> ORGANISM: Artificial
<220> FEATURE:
<223> OTHER INFORMATION: PNA modified oligonucleotide
<220> FEATURE:
<221> NAME/KEY: misc_feature
<222> LOCATION: (1)..(14)
<223> OTHER INFORMATION: PNA modified oligonucleotide, human acetyl-CoA
      carboxylase2 targeted artificial sequence
<220> FEATURE:
<221> NAME/KEY: misc_feature
<222> LOCATION: (1)..(1)
<223> OTHER INFORMATION: Carbamated N-terminal
<220> FEATURE:
<221> NAME/KEY: modified_base
<222> LOCATION: (3)..(3)
<223> OTHER INFORMATION: n is a, g, c, or t
<220> FEATURE:
<221> NAME/KEY: modified_base
<222> LOCATION: (5)..(5)
<223> OTHER INFORMATION: n is a, g, c, or t
<220> FEATURE:
<221> NAME/KEY: modified_base
<222> LOCATION: (7)..(7)
<223> OTHER INFORMATION: n is a, g, c, or t
<220> FEATURE:
<221> NAME/KEY: modified_base
<222> LOCATION: (9)..(9)
<223> OTHER INFORMATION: n is a, g, c, or t
<220> FEATURE:
<221> NAME/KEY: modified_base
<222> LOCATION: (11)..(11)
<223> OTHER INFORMATION: n is a, g, c, or t
<220> FEATURE:
<221> NAME/KEY: modified_base
<222> LOCATION: (13)..(13)
<223> OTHER INFORMATION: n is a, g, c, or t

<400> SEQUENCE: 6
ctnangnant ngnc                                                        14

<210> SEQ ID NO 7
<211> LENGTH: 18
<212> TYPE: RNA
<213> ORGANISM: Homo sapiens

<400> SEQUENCE: 7
ggccauuucg ucaguauc                                                    18

<210> SEQ ID NO 8
<211> LENGTH: 30
<212> TYPE: RNA
<213> ORGANISM: Homo sapiens

<400> SEQUENCE: 8
```
ggaagaggcc auuucgucag uaucuccuuc                                     30

<210> SEQ ID NO 9
<211> LENGTH: 19
<212> TYPE: DNA
<213> ORGANISM: Artificial
<220> FEATURE:
<223> OTHER INFORMATION: Synthetic primer

<400> SEQUENCE: 9
ttttccgaca agtgcagag                                                 19

<210> SEQ ID NO 10
<211> LENGTH: 18
<212> TYPE: DNA
<213> ORGANISM: Artificial
<220> FEATURE:
<223> OTHER INFORMATION: Synthetic primer

<400> SEQUENCE: 10
aacgtccaca atgttcag                                                  18

<210> SEQ ID NO 11
<211> LENGTH: 19
<212> TYPE: DNA
<213> ORGANISM: Artificial
<220> FEATURE:
<223> OTHER INFORMATION: Synthetic primer

<400> SEQUENCE: 11
gagtacttat acagccagg                                                 19

<210> SEQ ID NO 12
<211> LENGTH: 18
<212> TYPE: DNA
<213> ORGANISM: Artificial
<220> FEATURE:
<223> OTHER INFORMATION: Synthetic primer

<400> SEQUENCE: 12
ttctgaacat cgcgtctg                                                  18

<210> SEQ ID NO 13
<211> LENGTH: 16
<212> TYPE: RNA
<213> ORGANISM: Homo sapiens

<400> SEQUENCE: 13
gccauuucgu caguau                                                    16

ACETYL-COA CARBOSYLASE2 ANTISENSE OLIGONUCLEOTIDES

CROSS REFERENCE TO RELATED APPLICATIONS

This application is a national stage application under 35 U.S.C. § 371 of International Application No. PCT/KR2019/009697, filed on Aug. 5, 2019, which claims priority of Korean Application No. 10-2018-0095124, filed on Aug. 14, 2018, which are hereby incorporated by reference in their entirety.

SEQUENCE LISTING

The instant application contains an electronic sequence listing. The contents of the electronic sequence listing (ASCII; H2594334.txt; Size: 6,633 bytes; and Date of Creation: Feb. 22, 2023) is herein incorporated by reference in its entirety.

TECHNICAL FIELD

This invention relates to peptide nucleic acid derivatives complementarily targeting the human acetyl-CoA carboxylase2 pre-mRNA for improvement of skin aging mediated by acetyl-CoA carboxylase2.

BACKGROUND ART

Skin aging has received considerable attention since the signs of aging are most visible in the skin. Skin aging begins in their middle or late twenties with the reduction of collagen and elastin in the skin to result in dry and low elastic skin and even wrinkles. Obesity is a kind of inflammation reaction caused by the decline in blood circulation came from excessively deposited internal fat. Internal fat on blood vessel inhibits blood circulation and secretion of various hormones to promote aging in the whole body including the skin. In that sense, health conditions and diseases linked to obesity have to be monitored to get healthy and beautiful skin.

The biosynthesis and degradation of fatty acids are well regulated according to the physiological conditions to meet the demand of the body. Acetyl-CoA carboxylase (ACC) is a biotin-dependent enzyme that catalyzes the carboxylation of acetyl-CoA to produce malonyl-CoA, which is the rate-determining step in the first stage of fatty acid biosynthesis (FIG. 12).

ACC has a function of controlling metabolism of fatty acids in two ways. The most important function of ACC is to provide the malonyl-CoA substrate as a new building block in its active state for the fatty acid biosynthesis. Another function is to block the oxidation of fatty acids in mitochondria through inhibition of acyl group transfer of fatty acids.

In human, two main isoforms of ACC are expressed, acetyl-CoA carboxylase 1 (ACC1, ACACA, acetyl-CoA carboxylase alpha) and acetyl-CoA carboxylase 2 (ACC2, ACACB, acetyl-CoA carboxylase beta). Two ACCs have different functions each other, i.e., ACC maintains regulation of fatty acid synthesis whereas ACC2 mainly regulates fatty acid oxidation.

ACCs regulating biosynthesis and oxidation of fatty acids are potential targets for the treatment of many diseases such as new antibiotics utilizing the structure differences of bacteria and human ACCs, metabolic syndrome of diabetics and obesity, lipogenesis related growth inhibitors of cancer cell, and so on [Recent Patents Cardiovasc. Drug Discov. Vol 2, 162-80 (2007); PLoS One Vol 12, e0169566 (2017)].

Among them, a study on the $ACC2^{-/-}$ mutant mice has attracted lots of attention, where ACC2-deficient mice had lower level of fat with a higher fatty acid oxidation rate, lost or maintained body weight in spite of more food consumption, and had reduced risk of diabetes [Science Vol 291, 2613-6 (2001)]. These results suggested the possibility of ACC2 inhibitors to have a therapeutic effect on obesity and diabetes. In addition, treatment of the inhibitors to the skin may expect the effect of fat removal and eventually the prevention of obesity in the skin and the improvement of skin aging.

Considering the significance of obesity in skin aging process, it is very interesting and necessary to develop ACC2 inhibitors or the pharmaceuticals or cosmetics based on the mechanism of ACC2 expression, which may improve and prevent skin aging condition.

Pre-mRNA: Genetic information is carried on DNA (2-deoxyribose nucleic acid). DNA is transcribed to produce pre-mRNA (pre-messenger ribonucleic acid) in the nucleus. Mammalian pre-mRNA usually consists of exons and introns, and exon and intron are interconnected to each other as schematically provided. Exons and introns are numbered as exemplified in FIG. 13 which shows the structure of Pre-mRNA.

Splicing of Pre-mRNA: Pre-mRNA is processed into mRNA following deletion of introns by a series of complex reactions collectively called "splicing" which is schematically summarized in FIG. 14 [Ann. Rev. Biochem. 72(1), 291-336 (2003); Nature Rev. Mol. Cell Biol. 6(5), 386-398 (2005); Nature Rev. Mol. Cell Biol. 15(2), 108-121 (2014)].

Splicing is initiated by forming "spliceosome E complex" (i.e. early spliceosome complex) between pre-mRNA and splicing adapter factors. In "spliceosome E complex", U1 binds to the junction of exon N and intron N, and $U2AF^{35}$ binds to the junction of intron N and exon (N+1). Thus the junctions of exon/intron or intron/exon are critical to the formation of the early spliceosome complex. "Spliceosome E complex" evolves into "spliceosome A complex" upon additional complexation with U2. The "spliceosome A complex" undergoes a series of complex reactions to delete or splice out the intron to adjoin the neighboring exons.

Ribosomal Protein Synthesis: Proteins are encoded by DNA (2-deoxyribose nucleic acid). In response to cellular stimulation or spontaneously, DNA is transcribed to produce pre-mRNA (pre-messenger ribonucleic acid) in the nucleus. The introns of pre-mRNA are enzymatically spliced out to yield mRNA (messenger ribonucleic acid), which is then translocated into the cytoplasm. In the cytoplasm, a complex of translational machinery called ribosome binds to mRNA and carries out the protein synthesis as it scans the genetic information encoded along the mRNA [Biochemistry vol 41, 4503-4510 (2002); Cancer Res. vol 48, 2659-2668 (1988)].

Antisense Oligonucleotide (ASO): An oligonucleotide binding to nucleic acid including DNA, mRNA and premRNA in a sequence specific manner (i.e. complementarily) is called antisense oligonucleotide (ASO).

If an ASO tightly binds to an mRNA in the cytoplasm, for example, the ASO may be able to inhibit the ribosomal protein synthesis along the mRNA. ASO needs to be present within the cytoplasm in order to inhibit the ribosomal protein synthesis of its target protein.

Antisense Inhibition of Splicing: If an ASO tightly binds to a pre-mRNA in the nucleus, the ASO may be able to inhibit or modulate the splicing of pre-mRNA into mRNA. ASO needs to be present within the nucleus in order to inhibit or modulate the splicing of pre-mRNA into mRNA. Such antisense inhibition of splicing produces an mRNA or mRNAs lacking the exon targeted by the ASO. Such mRNA(s) is called "splice variant(s)", and encodes protein(s) smaller than the protein encoded by the full-length mRNA.

In principle, splicing can be interrupted by inhibiting the formation of "spliceosome E complex". If an ASO tightly binds to a junction of (5'→3') exon-intron, i.e. "5' splice site", the ASO blocks the complex formation between pre-mRNA and factor U1, and therefore the formation of "spliceosome E complex". Likewise, "spliceosome E complex" cannot be formed if an ASO tightly binds to a junction of (5'→3') intron-exon, i.e. "3' splice site".

3' splice site and 5' splice site are schematically illustrated in FIG. 15.

Unnatural Oligonucleotides: DNA or RNA oligonucleotides are susceptible to degradation by endogenous nucleases, limiting their therapeutic utility. To date, many types of unnatural (naturally non-occurring) oligonucleotides have been developed and studied intensively [*Clin. Exp. Pharmacol. Physiol.* vol 33, 533-540 (2006)]. Some of them show extended metabolic stability compared to DNA and RNA. Provided below are the chemical structures for a few of representative unnatural oligonucleotides. Such oligonucleotides predictably bind to a complementary nucleic acid as DNA or RNA does.

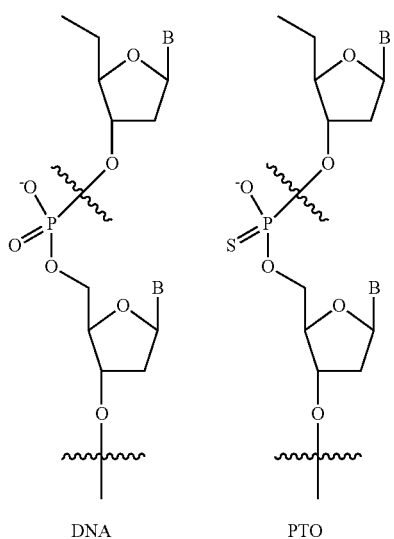

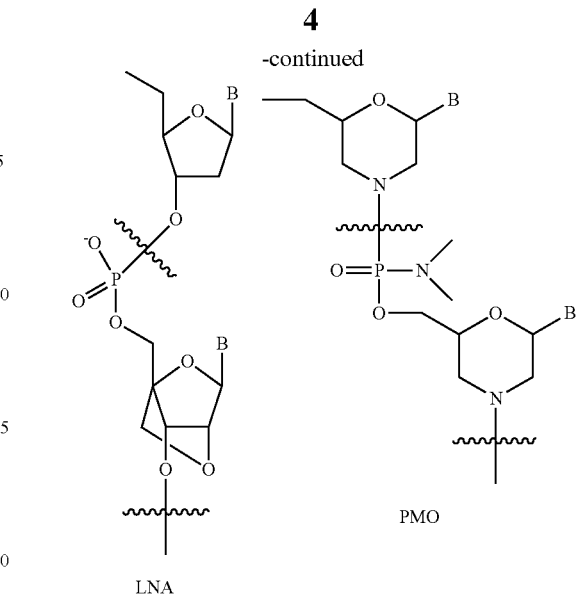

-continued

LNA

PMO

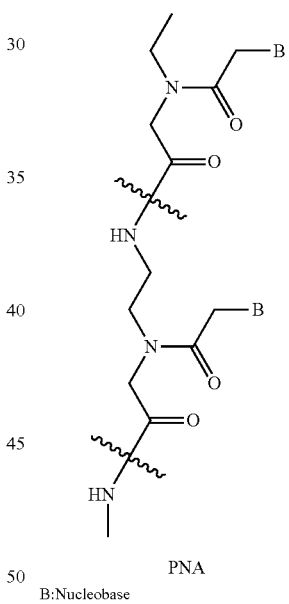

PNA

B:Nucleobase

Phosphorothioate Oligonucleotide: Phosphorothioate oligonucleotide (PTO) is a DNA analog with one of the backbone phosphate oxygen atoms replaced with a sulfur atom per monomer. Such a small structural change made PTO comparatively resistant to degradation by nucleases [*Ann. Rev. Biochem.* vol 54, 367-402 (1985)].

Reflecting the structural similarity in the backbone of PTO and DNA, they both poorly penetrate the cell membrane in most mammalian cell types. For some types of cells abundantly expressing transporter(s) of DNA, however, DNA and PTO show good cell penetration. Systemically administered PTOs are known to readily distribute to the liver and kidney [*Nucleic Acids Res.* vol 25, 3290-3296 (1997)].

In order to facilitate PTO's cell penetration in vitro, lipofection has been popularly practiced. However, lipofection physically alters the cell membrane, causes cytotoxicity, and therefore would not be ideal for long term in vivo therapeutic use.

Over the past 30 years, antisense PTOs and variants of PTOs have been clinically evaluated to treat cancers, immunological disorders, metabolic diseases, and so on [*Biochemistry* vol 41, 4503-4510 (2002); *Clin. Exp. Pharmacol. Physiol.* vol 33, 533-540 (2006)]. Many of such antisense drug candidates have not been successfully developed partly due to PTO's poor cell penetration. In order to overcome the poor cell penetration, PTO needs to be administered at high dose for therapeutic activity. However, PTOs are known to be associated with dose-limiting toxicity including increased coagulation time, complement activation, tubular nephropathy, Kupffer cell activation, and immune stimulation including splenomegaly, lymphoid hyperplasia, mononuclear cell infiltration [*Clin. Exp. Pharmacol. Physiol.* vol 33, 533-540 (2006)].

Many antisense PTOs have been found to show due clinical activity for diseases with a significant contribution from the liver or kidney. Mipomersen is a PTO analog which inhibits the synthesis of apoB-100, a protein involved in LDL cholesterol transport. Mipomersen manifested due clinical activity in atherosclerosis patients most likely due to its preferential distribution to the liver [*Circulation* vol 118(7), 743-753 (2008)]. ISIS-113715 is a PTO antisense analog inhibiting the synthesis of protein tyrosine phosphatase 1B (PTP1B), and was found to show therapeutic activity in type II diabetes patients. [*Curr. Opin. Mol. Ther.* vol 6, 331-336 (2004)].

Locked Nucleic Acid: In locked nucleic acid (LNA), the backbone ribose ring of RNA is structurally constrained to increase the binding affinity for RNA or DNA. Thus, LNA may be regarded as a high affinity DNA or RNA analog [*Biochemistry* vol 45, 7347-7355 (2006)].

Phosphorodiamidate Morpholino Oligonucleotide: In phosphorodiamidate morpholino oligonucleotide (PMO), the backbone phosphate and 2-deoxyribose of DNA are replaced with phosphoramidate and morpholine, respectively [*Appl. Microbiol. Biotechnol.* vol 71, 575-586 (2006)]. Whilst the DNA backbone is negatively charged, the PMO backbone is not charged. Thus the binding between PMO and mRNA is free of electrostatic repulsion between the backbones, and tends to be stronger than that between DNA and mRNA. Since PMO is structurally very different from DNA, PMO wouldn't be recognized by the hepatic transporter recognizing DNA. PMO may exhibit a different tissue distribution than PTO, but PMO, like PTO, doesn't readily penetrate the cell membrane.

Peptide Nucleic Acid: Peptide nucleic acid (PNA) is a polypeptide with N-(2-aminoethyl)glycine as the unit backbone, and was discovered by Dr. Nielsen and colleagues [*Science* vol 254, 1497-1500 (1991)]. The chemical structure and abbreviated nomenclature of PNA are illustrated in the drawing provided below. Like DNA and RNA, PNA also selectively binds to complementary nucleic acid. [*Nature (London)* vol 365, 566-568 (1992)]. In binding to complementary nucleic acid, the N-terminus of PNA is regarded as equivalent to the "5'-end" of DNA or RNA, and the C-terminus of PNA as equivalent to the "3'-end" of DNA or RNA.

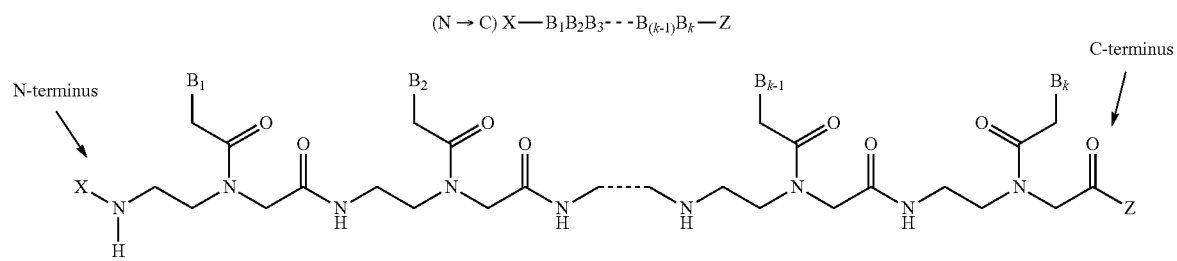

Like PMO, the PNA backbone is not charged. Thus the binding between PNA and RNA tends to be stronger than the binding between DNA and RNA. Since PNA is markedly different from DNA in the chemical structure, PNA wouldn't be recognized by the hepatic transporter(s) recognizing DNA, and would show a tissue distribution profile different from that of DNA or PTO. However, PNA also poorly penetrates the mammalian cell membrane [*Adv. Drug Delivery Rev.* vol 55, 267-280 (2003)].

Modified Nucleobases to Improve Membrane Permeability of PNA: PNA was made highly permeable to mammalian cell membrane by introducing modified nucleobases with a cationic lipid or its equivalent covalently attached thereto. The chemical structures of such modified nucleobases are provided below. Such modified nucleobases of cytosine, adenine, and guanine were found to predictably and complementarily hybridize with guanine, thymine, and cytosine, respectively [PCT Appl. No. PCT/KR2009/001256; EP2268607; U.S. Pat. No. 8,680,253].

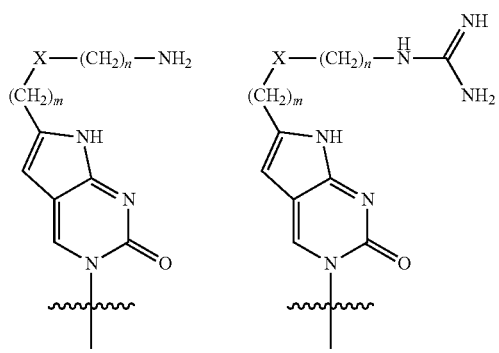

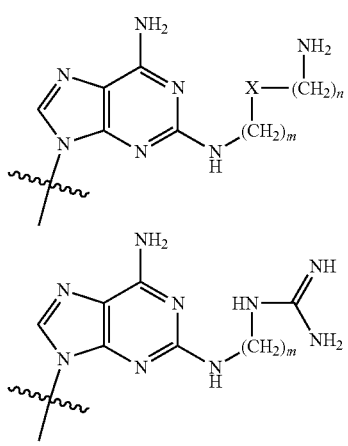

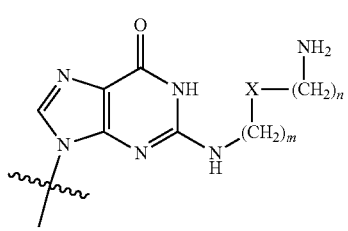

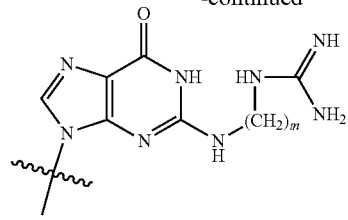

X = $CH_2$, O, S, or NH
m = integer
n = integer

Incorporation of such modified nucleobases onto PNA resembles situations of lipofection. By lipofection, oligonucleotide molecules with phosphate backbone are wrapped with cationic lipid molecules such as lipofectamine, and such lipofectamine/oligonucleotide complexes tend to penetrate membrane rather easily as compared to naked oligonucleotide molecules.

In addition to good membrane permeability, those PNA derivatives were found to possess ultra-strong affinity for complementary nucleic acid. For example, introduction of 4 to 5 modified nucleobases onto 11- to 13-mer PNA derivatives easily yielded a $T_m$ gain of 20° C. or higher in duplex formation with complementary DNA. Such PNA derivatives are highly sensitive to a single base mismatch. A single base mismatch resulted in a $T_m$ loss of 11 to 22° C. depending on the type of modified base as well as PNA sequence.

Small Interfering RNA (siRNA): Small interfering RNA (siRNA) refers to a double stranded RNA of 20-25 base pairs [*Microbiol. Mol. Biol. Rev.* vol 67(4), 657-685 (2003)]. The antisense strand of siRNA somehow interacts with proteins to form an "RNA-induced Silencing Complex" (RISC). Then the RISC binds to a certain portion of mRNA complementary to the antisense strand of siRNA. The mRNA complexed with the RISC undergoes cleavage. Thus siRNA catalytically induces the cleavage of its target mRNA, and consequently inhibits the protein expression by the mRNA. The RISC does not always bind to the full complementary sequence within its target mRNA, which raises concerns relating to off-target effects of an siRNA therapy. Like other classes of oligonucleotide with DNA or RNA backbone, siRNA possesses poor cell permeability and therefore tends to show poor in vitro or in vivo therapeutic activity unless properly formulated or chemically modified to have good membrane permeability.

ACC siRNA: The mixture of ACC1 siRNA and ACC2 siRNA was reported to inhibit the expression of ACC1 and ACC2 mRNAs and proteins in glioblastoma cancer cell line following a lipofection at 20 nM each [PLoS One Vol 12, e0169566 (2017)]. These results may be useful to the study of ACC related lipogenic cancer metastasis.

DISCLOSURE OF THE INVENTION

Problem to be Solved

Since obesity has a profound effect on skin aging, health conditions and diseases linked to obesity have to be monitored to get healthy and beautiful skin.

A study on the ACC2−/− mutant mice with respect to obesity has attracted lots of attention.

In addition, although ACCs siRNA were reported to inhibit the expression of ACCs mRNAs and proteins in cancer cell line, siRNAs are too expensive to manufacture and develop as anti-aging agent for skin to say nothing of their delivery challenge into the skin. Therefore, it is necessary to develop the pharmaceuticals or cosmetics based on the mechanism of ACC2 expression, which may improve and prevent skin aging condition.

Solution to the Problem

The present invention provides a peptide nucleic acid (PNA) derivative represented by Formula I, or a pharmaceutically acceptable salt thereof.

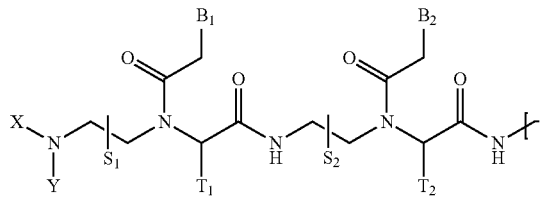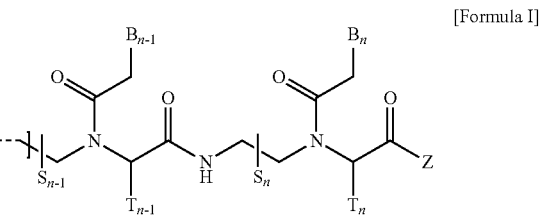

[Formula I]

wherein, n is an integer between 10 and 21;

the compound of Formula I possesses at least a 10-mer complementary overlap with the 18-mer pre-mRNA sequence of [(5'-, 3') GGCCAUUUCGUCAGUAUC] (SEQ. NO. 7) in the human ACC2 pre-mRNA;

the compound of Formula I is fully complementary to the human ACC2 pre-mRNA, or partially complementary to the human ACC2 pre-mRNA with one or two mismatches;

$S_1$, $S_2$, . . . , $S_{n-1}$, $S_n$, $T_1$, $T_2$, . . . , $T_{n-1}$, and $T_n$ independently represent hydrido, deuterido, substituted or non-substituted alkyl, or substituted or non-substituted aryl radical;

X and Y independently represent hydrido, deuterido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkyloxy, substituted or non-substituted aryloxy, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl, or substituted or non-substituted arylphosphonyl radical;

Z represents hydrido, deuterido, hydroxy, substituted or non-substituted alkyloxy, substituted or non-substituted aryloxy, substituted or non-substituted amino, substituted or non-substituted alkyl, or substituted or non-substituted aryl radical;

$B_1$, $B_2$, . . . , $B_{n-1}$, and $B_n$ are independently selected from natural nucleobases including adenine, thymine, guanine, cytosine and uracil, and unnatural nucleobases; and, at least four of $B_1$, $B_2$, . . . , $B_{n-1}$, and $B_n$ are independently selected from unnatural nucleobases with a substituted or non-substituted amino radical covalently linked to the nucleobase moiety.

The compound of Formula I induces the skipping of "exon 12" in the human ACC2 pre-mRNA, yields the human ACC2 mRNA splice variant(s) lacking "exon 12", and therefore is useful to inhibit the functional activity of the gene transcribing the human ACC2 pre-mRNA.

The condition that "n is an integer between 10 and 21" literally means that n is an integer selectable from a group of integers of 11, 12, 13, 14, 15, 16, 17, 18, 19, and 20.

The chemical structures of natural or unnatural nucleobases in the PNA derivative of Formula I are exemplified in FIGS. 1a-1c. Natural (i.e. naturally occurring) or unnatural (naturally non-occurring) nucleobases of this invention comprise but are not limited to the nucleobases provided in FIGS. 1a-1c. Provision of such unnatural nucleobases is to illustrate the diversity of allowable nucleobases, and therefore should not be interpreted to limit the scope of the present invention.

The substituents adopted to describe the PNA derivative of Formula I are exemplified in FIGS. 2a-2e. FIG. 2a provides examples for substituted or non-substituted alkyl radicals. Substituted or non-substituted alkylacyl and substituted or non-substituted arylacyl radicals are exemplified in FIG. 2b. FIG. 2c illustrates examples for substituted or non-substituted alkylamino, substituted or non-substituted arylamino, substituted or non-substituted aryl, substituted or non-substituted alkylsulfonyl or arylsulfonyl, and substituted or non-substituted alkylphosphonyl or arylphosphonyl radicals. FIG. 2d provides examples for substituted or non-substituted alkyloxycarbonyl or aryloxycarbonyl, substituted or non-substituted alkyl aminocarbonyl or arylaminocarbonyl radicals. In FIG. 2e are provided examples for substituted or non-substituted alkylaminothiocarbonyl, substituted or non-substituted arylaminothiocarbonyl, substituted or non-substituted alkyloxythiocarbonyl, and substituted or non-substituted aryloxythiocarbonyl radicals. Provision of such exemplary substituents is to illustrate the diversity of allowable substituents, and therefore should not be interpreted to limit the scope of the present invention. A skilled person in the field may easily figure out that oligonucleotide sequence is the overriding factor for sequence specific binding of oligonucleotide to the target pre-mRNA sequence over substituents in the N-terminus or C-terminus.

The compound of Formula I tightly binds to the complementary DNA as exemplified in the prior art [PCT/KR2009/001256]. The duplex between the PNA derivative of Formula I and its full-length complementary DNA or RNA possesses a $T_m$ value too high to be reliably determined in aqueous buffer. The PNA compound of Formula I yields high $T_m$ values with complementary DNAs of shorter length.

The compound of Formula I complementarily binds to the 5' splice site of "exon 12" of the human ACC2 pre-mRNA. [NCBI Reference Sequence: NG_046907]. The 16-mer sequence of [(5'→3') GCCAUUUCGUCAGUAU] (SEQ. NO. 13) spans the junction of "exon 12" and "intron 12" in the human ACC2 pre-mRNA, and consists of 8-mer from "exon 12" and 8-mer from "intron 12". Thus the 16-mer pre-mRNA sequence may be conventionally denoted as

[(5'→3') GCCAUUUC|gucaguau], wherein the exon and intron sequence are provided as "capital" and "small" letters, respectively, and the exon-intron junction is expressed with "|". The conventional denotation for pre-mRNA is further illustrated by a 30-mer sequence of [(5'→3') GGAAGAGGCCAUUUC|gucaguaucuccuuc] (SEQ. NO. 8) spanning the junction of "exon 12" and "intron 12" in the human ACC2 pre-mRNA.

The compound of Formula I tightly binds to the target 5' splice site of the human ACC2 pre-mRNA transcribed from the human ACC2 gene, and interferes with the formation of "spliceosome early complex" to yield ACC2 mRNA splice variant(s) lacking "exon 12" (exon 12 skipping).

The strong RNA affinity allows the compound of Formula I to induce the skipping of ACC2 "exon 12", even when the PNA derivative possesses one or two mismatches with the target 5' splice site in the ACC2 pre-mRNA. Similarly the PNA derivative of Formula I may still induce the skipping of ACC2 "exon 12" in a ACC2 mutant pre-mRNA possessing one or two SNPs (single nucleotide polymorphism) in the target splice site.

The compound of Formula I possesses good cell permeability and can be readily delivered into cell as "naked" oligonucleotide as exemplified in the prior art [PCT/KR2009/001256]. Thus the compound of this invention induces the skipping of "exon 12" in the ACC2 pre-mRNA, and yields ACC2 mRNA splice variant(s) lacking ACC2 "exon 12" in cells treated with the compound of Formula I as "naked" oligonucleotide. The compound of Formula I does not require any means or formulations for delivery into cell to potently induce the skipping of the target exon in cells. The compound of Formula I readily induces the skipping of ACC2 "exon 12" in cells treated with the compound of this invention as "naked" oligonucleotide at sub-femtomolar concentration.

Owing to the good cell or membrane permeability, the PNA derivative of Formula I can be topically administered as "naked" oligonucleotide to induce the skipping of ACC2 "exon 12" in the skin. The compound of Formula I does not require a formulation to increase trans-dermal delivery into target tissue for the intended therapeutic or biological activity. Usually the compound of Formula I is dissolved in water and co-solvent, and topically or trans-dermally administered at subpicomolar concentration to elicit the desired therapeutic or biological activity in target skin. The compound of this invention does not need to be heavily or invasively formulated to elicit the topical therapeutic activity. Nevertheless, the PNA derivative of Formula I can be formulated with cosmetic ingredients or adjuvants as topical cream or lotion. Such topical cosmetic cream or lotion may be useful to treat skin aging.

The compound of the present invention can be topically administered to a subject at a therapeutically or biologically effective concentration ranging from 1 aM to higher than 1 nM, which would vary depending on the dosing schedule, conditions or situations of the subject, and so on.

The PNA derivative of Formula I can be variously formulated including but not limited to injections, nasal spray, transdermal patch, and so on. In addition, the PNA derivative of Formula I can be administered to the subject at therapeutically effective dose and the dose of administration can be diversified depending on indication, administration route, dosing schedule, conditions or situations of the subject, and so on.

The compound of Formula I may be used as combined with a pharmaceutically acceptable acid or base including but not limited to sodium hydroxide, potassium hydroxide, hydrochloric acid, methanesulfonic acid, citric acid, trifluoroacetic acid, and so on.

The PNA derivative of Formula I or a pharmaceutically acceptable salt thereof can be administered to a subject in combination with a pharmaceutically acceptable adjuvant including but not limited to citric acid, hydrochloric acid, tartaric acid, stearic acid, polyethyleneglycol, polypropyleneglycol, ethanol, isopropanol, sodium bicarbonate, distilled water, preservative(s), and so on.

Of interest is a PNA derivative of Formula I, or a pharmaceutically acceptable salt thereof:
wherein,
n is an integer between 10 and 21;
the compound of Formula I possesses at least a 10-mer complementary overlap with the 18-mer pre-mRNA sequence of [(5'→3') GGCCAUUUCGUCAGUAUC] (SEQ. NO. 7) in the human ACC2 pre-mRNA;
the compound of Formula I is fully complementary to the human ACC2 pre-mRNA, or partially complementary to the human ACC2 pre-mRNA with one or two mismatches;
$S_1, S_2, \ldots, S_{n-1}, S_n, T_1, T_2, \ldots, T_{n-1}$, and $T_n$ independently represent hydrido, deuterido radical;
X and Y independently represent hydrido, deuterido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkyloxy, substituted or non-substituted aryloxy, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl, or substituted or non-substituted arylphosphonyl radical;

Z represents hydrido, hydroxy, substituted or non-substituted alkyloxy, substituted or non-substituted aryloxy, or substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV:

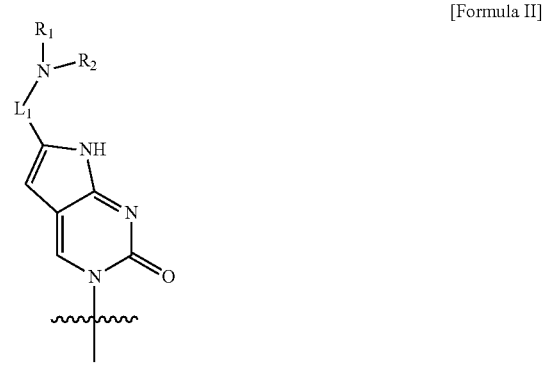

[Formula II]

-continued

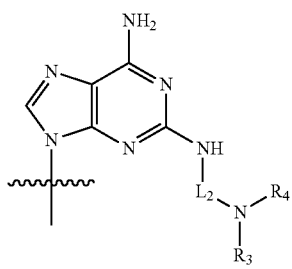

[Formula III]

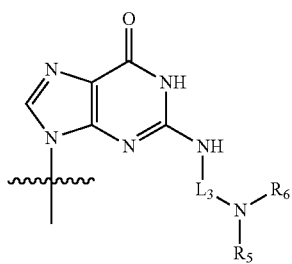

[Formula IV]

wherein, $R_1$, $R_2$, $R_3$, $R_4$, $R_5$ and $R_6$ are independently selected from hydrido and substituted or non-substituted alkyl radical;

$L_1$, $L_2$ and $L_3$ are a covalent linker represented by Formula V covalently linking the basic amino group to the nucleobase moiety:

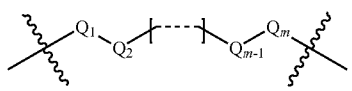

[Formula V]

wherein, $Q_1$ and $Q_m$ are substituted or non-substituted methylene (—$CH_2$—) radical, and $Q_m$ is directly linked to the basic amino group;

$Q_2$, $Q_3$, . . . , and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 15.

Of high interest is a PNA oligomer of Formula I, or a pharmaceutically acceptable salt thereof:

wherein, n is an integer between 11 and 16;

the compound of Formula I possesses at least a 10-mer complementary overlap with the 18-mer pre-mRNA sequence of [(5'→3') GGCCAUUUCGUCAGUAUC] (SEQ. NO. 7) in the human ACC2 pre-mRNA;

the compound of Formula I is fully complementary to the human ACC2 pre-mRNA;

$S_1$, $S_2$, . . . , $S_{n-1}$, $S_n$, $T_1$, $T_2$, . . . , $T_{n-1}$, and $T_n$ are hydrido radical;

X and Y independently represent hydrido, substituted or non-substituted alkylacyl, or substituted or non-substituted alkyloxycarbonyl radical;

Z represents substituted or non-substituted amino radical;

$B_1$, $B_2$, . . . , $B_{n-1}$, and $B_n$ are independently selected from natural nucleobases including adenine, thymine, guanine, cytosine and uracil, and unnatural nucleobases;

at least five of $B_1$, $B_2$, . . . , $B_{n-1}$, and $B_n$ are independently selected from unnatural nucleobases represented by Formula II, Formula III, or Formula IV;

$R_1$, $R_2$, $R_3$, $R_4$, $R_5$ and $R_6$ are hydrido radical;

$Q_1$ and $Q_m$ are methylene radical, and $Q_m$ is directly linked to the basic amino group;

$Q_2$, $Q_3$, . . . , and $Q_{m-1}$ are independently selected from methylene and oxygen radical; and, m is an integer between 1 and 9.

Of higher interest is a PNA derivative of Formula I, or a pharmaceutically acceptable salt thereof:

wherein, n is an integer between 11 and 16;

the compound of Formula I possesses at least a 10-mer complementary overlap with the 18-mer pre-mRNA sequence of [(5'→3') GGCCAUUUCGUCAGUAUC] (SEQ. NO. 7) in the human ACC2 pre-mRNA;

the compound of Formula I is fully complementary to the human ACC2 pre-mRNA;

$S_1$, $S_2$, . . . , $S_{n-1}$, $S_n$, $T_1$, $T_2$, . . . , $T_{n-1}$, and $T_n$ are hydrido radical;

X is hydrido radical;

Y represents substituted or non-substituted alkyloxycarbonyl radical;

Z represents substituted or non-substituted amino radical;

$B_1$, $B_2$, . . . , $B_{n-1}$, and $B_n$ are independently selected from natural nucleobases including adenine, thymine, guanine, cytosine and uracil, and unnatural nucleobases;

at least five of $B_1$, $B_2$, . . . , $B_{n-1}$, and $B_n$ are independently selected from unnatural nucleobases represented by Formula II, Formula III, or Formula IV;

$R_1$, $R_2$, $R_3$, $R_4$, $R_5$ and $R_6$ are hydrido radical;

$L_1$ represents —$(CH_2)_2$—O—$(CH_2)_2$—, —$CH_2$—O—$(CH_2)_2$—, —$CH_2$—O—$(CH_2)_3$—, —$CH_2$—O—$(CH_2)_4$—, or —$CH_2$—O—$(CH_2)_5$—; and, $L_2$ and $L_3$ are independently selected from —$(CH_2)_2$—O—$(CH_2)_2$—, —$(CH_2)_3$—O—$(CH_2)_2$—, —$(CH_2)_2$—O—$(CH_2)_3$—, —$(CH_2)_2$—, —$(CH_2)_3$—, —$(CH_2)_4$—, —$(CH_2)_5$—, —$(CH_2)_6$—, —$(CH_2)_7$—, and —$(CH_2)_8$—.

Of specific interest is a PNA derivative of Formula I which is selected from the group of compounds provided below (Hereinafter referred to as ASOs 1, 2, 3, 4, 5 and 6, respectively), or a pharmaceutically acceptable salt thereof:

(N→C) Fethoc-CTG(6)-ACG(6)-AA(5)A-TG(6)G-C(1O2)C—NH$_2$ (SEQ. NO. 1);

(N→C) Fethoc-TA(5)C(1O2)-TGA(5)-CGA(5)-AA(5)T-G(6)GC(1O2)-C—NH$_2$ (SEQ. NO. 2);

(N→C) Fethoc-TA(5)C-TG(5)A-C(1O2)GA(5)-AA(5)T-G(5)G-NH$_2$ (SEQ. NO. 3);

(N→C) Fethoc-AC(1O2)T-GA(5)C-GA(5)A-A(5)TG(5)-GC(1O2)-NH$_2$ (SEQ. NO. 4);

(N→C) Fethoc-CTG(6)-AC(1O2)G-A(5)AA(5)-TG(6)G-NH$_2$ (SEQ. NO. 5);

(N→C) Fethoc-CTG(6)-AC(1O2)G-A(5)AA(5)-TG(6)G-C(1O2)C—NH$_2$ (SEQ. NO. 6)

wherein,

A, G, T, and C are PNA monomers with a natural nucleobase of adenine, thymine, guanine and cytosine, respectively;

C(pOq), A(p), and G(p) are PNA monomers with an unnatural nucleobase represented by Formula VI, Formula VII, and Formula VIII, respectively;

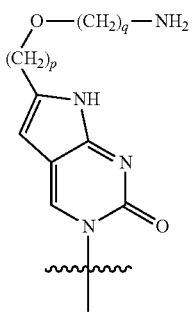

[Formula VI]

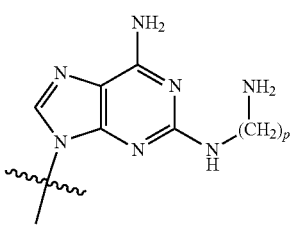

[Formula VII]

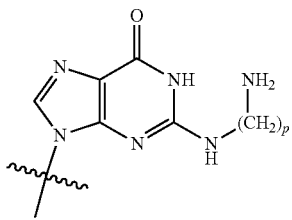

[Formula VIII]

wherein, p and q are integers, for example, p is 1 or 5 and q is 2 in case of ASO 4; and, "Fethoc-" is the abbreviation for "[2-(9-fluorenyl)ethyl-1-oxy]carbonyl" and "—NH$_2$" is for non-substituted "-amino" group.

FIG. 3 collectively and unambiguously provides the chemical structures for the PNA monomers abbreviated as A, G, T, C, C(pOq), A(p), and G(p). As discussed in the prior art [PCT/KR2009/001256], C(pOq) is regarded as a "modified cytosine" PNA monomer due to its hybridization for "guanine". A(p) is taken as "modified adenine" PNA monomers due to their hybridization for "thymine", and G(p) is taken as "modified guanine" PNA monomers due to their hybridization for "cytosine". In addition, in order to illustrate the abbreviations employed for such PNA derivatives, the chemical structure of ASO 1 "(N→C) CTG(6)-ACG(6)-AA(5)A-TG(6)G-C(1O2)C—NH$_2$" (SEQ. NO. 1) is provided in FIG. 4.

ASO 1 is equivalent to the DNA sequence of "(5'→3') CTG-ACG-AAA-TGG-CC" for complementary binding to pre-mRNA. The 14-mer PNA has a 14-mer complementary overlap with the 14-mer sequence marked "bold" and "underlined" within the 30-mer RNA sequence of (SEQ ID NO: 8)
[(5' → 3')GGAAGAGGCCAUUUC | gucaguaucuccuuc]

spanning the junction of "exon 12" and "intron 12" in the human ACC2 pre-mRNA.

In some embodiments, the present invention provides a method of treating conditions or disorders associated with human ACC2 gene transcription in a subject, comprising administering to the subject the peptide nucleic acid derivative of the present invention or a pharmaceutically acceptable salt thereof.

In some embodiments, the present invention provides a method of treating skin aging in a subject, comprising administering to the subject the peptide nucleic acid derivative of the present invention or a pharmaceutically acceptable salt thereof.

In some embodiments, the present invention provides a pharmaceutical composition for treating conditions or disorders associated with human ACC2 gene transcription, comprising the peptide nucleic acid derivative of the present invention or a pharmaceutically acceptable salt thereof.

In some embodiments, the present invention provides a cosmetic composition for treating conditions or disorders associated with human ACC2 gene transcription, comprising the peptide nucleic acid derivative of the present invention or a pharmaceutically acceptable salt thereof.

In some embodiments, the present invention provides a pharmaceutical composition for treating skin aging, comprising the peptide nucleic acid derivative of the present invention or a pharmaceutically acceptable salt thereof.

In some embodiments, the present invention provides a cosmetic composition for treating skin aging, comprising the peptide nucleic acid derivative of the present invention or a pharmaceutically acceptable salt thereof.

Effect of Invention

Conditions or disorders associated with human ACC2 gene transcription can be treated by administering a PNA derivative of Formula I or a pharmaceutically acceptable salt thereof.

Skin aging can be treated by administering a PNA derivative of Formula I or a pharmaceutically acceptable salt thereof.

BRIEF EXPLANATION OF DRAWINGS

FIGS. 2a-2e. Examples of substituents selectable for the peptide nucleic acid derivative of Formula I.

FIG. 3. Chemical structures of PNA monomers with natural or modified nucleobase.

FIG. 5. Chemical structures of Fmoc-PNA monomers used to synthesize the PNA derivatives of this invention.

BEST MODE FOR CARRYING OUT THE INVENTION

General Procedures for Preparation of PNA Oligomers

PNA oligomers were synthesized by solid phase peptide synthesis (SPPS) based on Fmoc-chemistry according to the method disclosed in the prior art [U.S. Pat. No. 6,133,444; WO96/40685] with minor but due modifications. Fmoc is {(9-fluorenyl)methyloxy}carbonyl. The solid support employed in this study was H-Rink Amide-ChemMatrix purchased from PCAS BioMatrix Inc. (Quebec, Canada). Fmoc-PNA monomers with a modified nucleobase were synthesized as described in the prior art [PCT/KR 2009/001256] or with minor modifications. Such Fmoc-PNA monomers with a modified nucleobase and Fmoc-PNA monomers with a naturally occurring nucleobase were used to synthesize the PNA derivatives of the present invention. PNA oligomers were purified by Cis-reverse phase HPLC (water/acetonitrile or water/methanol with 0.1% TFA) and characterized by mass spectrometry including ESI/TOF/MS.

Figure 16:
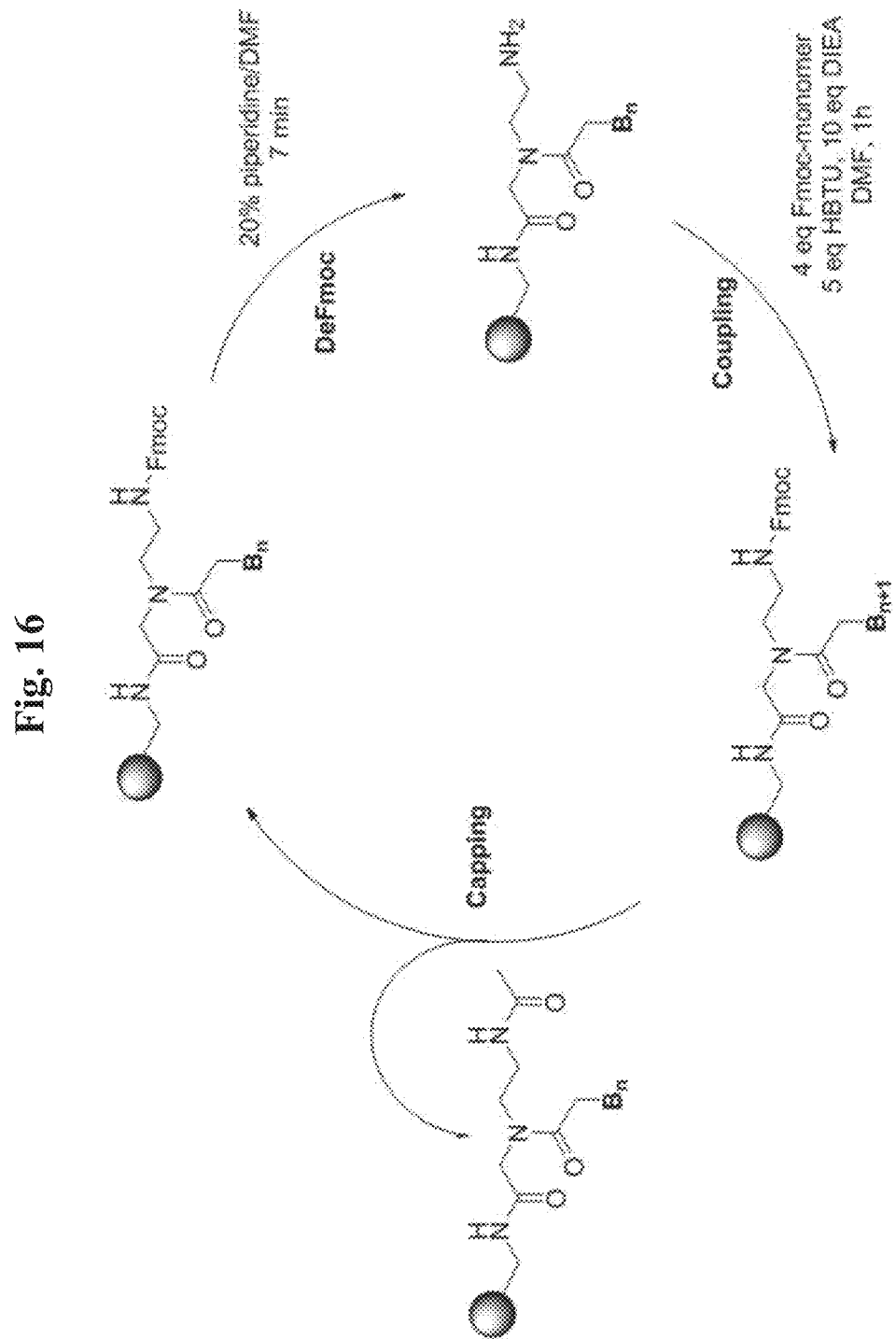
FIG. 16. Brief Illustration of the Scheme 1.

Scheme 1 illustrates a typical monomer elongation cycle adopted in the SPPS of this study, and the synthetic details are provided as below. To a skilled person in the field, however, there are lots of minor variations obviously possible in effectively running such SPPS reactions on an automatic peptide synthesizer or manual peptide synthesizer. Each reaction step in Scheme 1 is briefly provided in FIG. 16.

[Activation of H-Rink-ChemMatrix Resin] When the amine on the resin was not protected with Fmoc, 0.01 mmol (ca 20 mg resin) of the ChemMatrix resin in 1.5 mL 20% piperidine/DMF was vortexed in a libra tube for 20 min, and the DeFmoc solution was filtered off. The resin was washed for 30 sec each in series with 1.5 mL methylene chloride (MC), 1.5 mL dimethylformamide (DMF), 1.5 mL MC, 1.5 mL DMF, and 1.5 mL MC. The resulting free amines on the solid support were subjected to coupling with an Fmoc-PNA monomer.

[DeFmoc] When the amine on the resin was protected with Fmoc, the suspension of 0.01 mmol (ca 20 mg) of the resin in 1.5 mL 20% piperidine/DMF was vortexed for 7 min, and the DeFmoc solution was filtered off. The resin was washed for 30 sec each in series with 1.5 mL MC, 1.5 mL DMF, 1.5 mL MC, 1.5 mL DMF, and 1.5 mL MC. The resulting free amines on the solid support were immediately subjected to coupling with an Fmoc-PNA monomer.

[Coupling with Fmoc-PNA Monomer] The free amines on the solid support were coupled with an Fmoc-PNA monomer as follows. 0.04 mmol of PNA monomer, 0.05 mmol HBTU, and 0.1 mmol DIEA were incubated for 2 min in 1 mL anhydrous DMF, and added to the resin with free amines. The resin solution was vortexed for 1 hour and the reaction medium was filtered off. Then the resin was washed for 30 sec each in series with 1.5 mL MC, 1.5 mL DMF, and 1.5 mL MC. The chemical structures of Fmoc-PNA monomers with a modified nucleobase used in this invention are provided in FIG. 5. The Fmoc-PNA monomers with a modified nucleobase are provided in FIG. 5 should be taken as examples, and therefore should not be taken to limit the scope of the present invention. A skilled person in the field may easily figure out a number of variations in Fmoc-PNA monomers to synthesize the PNA derivative of Formula I.

[Capping] Following the coupling reaction, the unreacted free amines were capped by shaking for 5 min in 1.5 mL capping solution (5% acetic anhydride and 6% 2,6-leutidine in DMF). Then the capping solution was filtered off and washed for 30 sec each in series with 1.5 mL MC, 1.5 mL DMF, and 1.5 mL MC.

[Introduction of "Fethoc-" Radical in N-Terminus] "Fethoc-" radical was introduced to the N-terminus by reacting the free amine on the resin with "Fethoc-OSu" by the following method. The suspension of the resin in the solution of 0.1 mmol of Fethoc-OSu and 0.1 mmol DIEA in 1 mL anhydrous MDF was vortexed for 1 hr, and the solution was filtered off. The resin was washed for 30 sec each in series with 1.5 mL MC, 1.5 mL DMF, and 1.5 mL MC. The chemical structure of "Fethoc-OSu" [CAS No. 179337-69-0, $C_{20}H_{17}NO_5$, MW 351.36] used in the present invention is provided as follows.

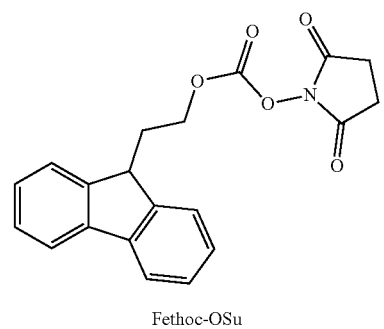 [SMILES: O=C(OCCC1c2ccccc2-c2ccccc21)ON1C(=O)CCC1=O]

Fethoc-OSu

[Cleavage from Resin] PNA oligomers bound to the resin were cleaved from the resin by shaking for 3 hours in 1.5 mL cleavage solution (2.5% tri-isopropylsilane and 2.5% water in trifluoroacetic acid). The resin was filtered off and the filtrate was concentrated under reduced pressure. The resulting residue was triturated with diethyl ether and the resulting precipitate was collected by filtration for purification by reverse phase HPLC.

Figure 1A:
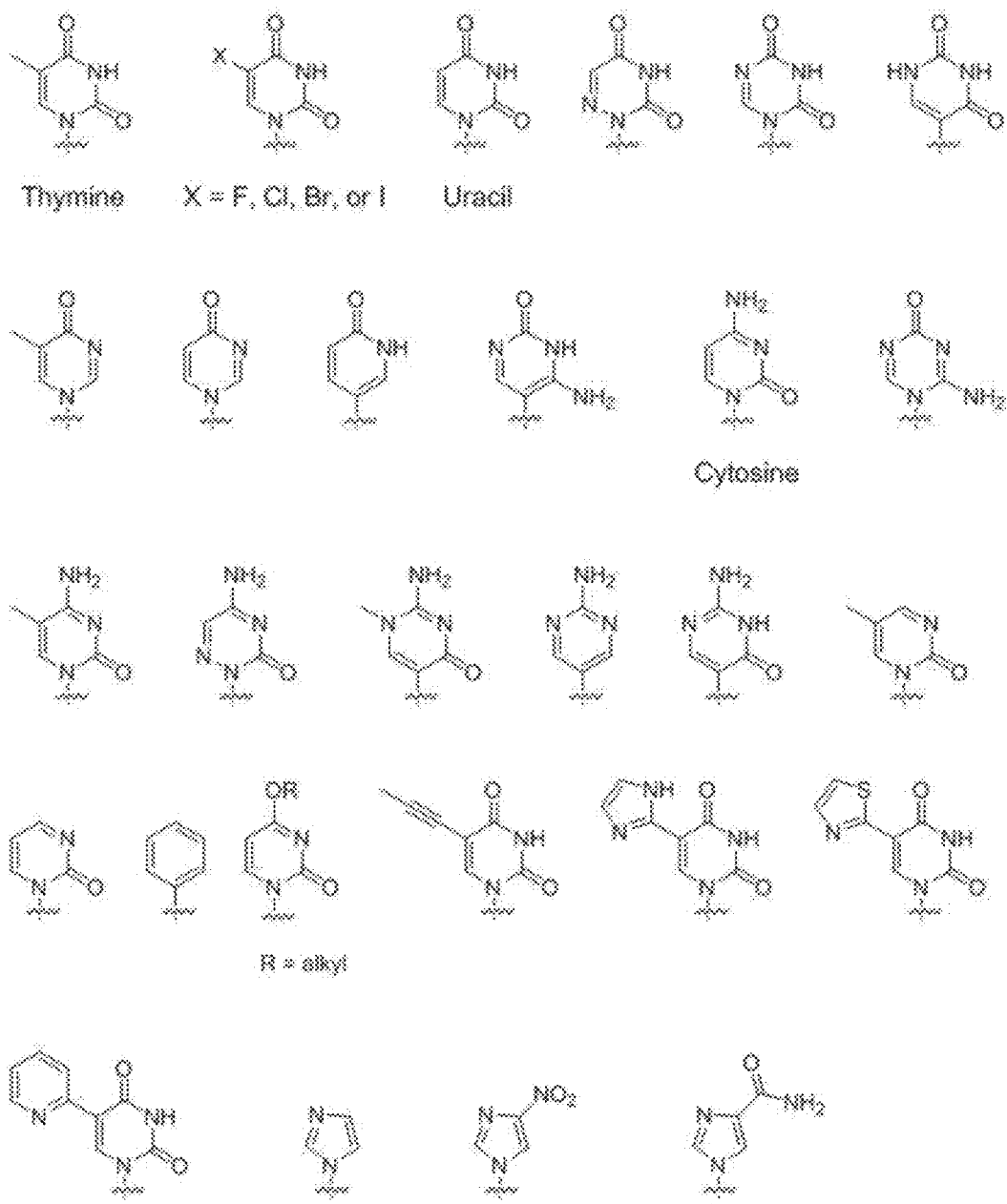
FIGS. 1a-1c. Examples of natural or unnatural (modified) nucleobases selectable for the peptide nucleic acid derivative of Formula I.
Figure 1B:
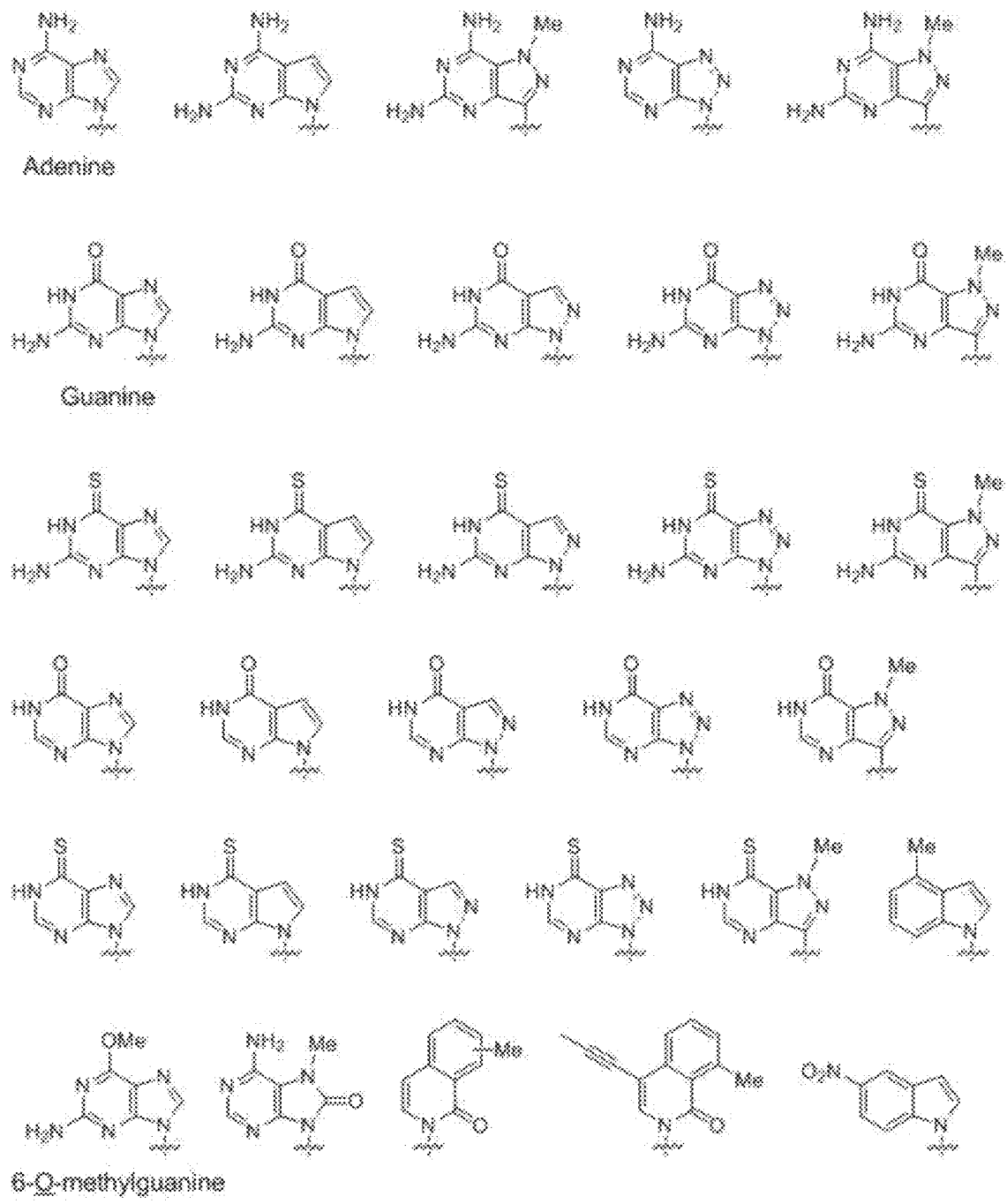
Figure 1C:
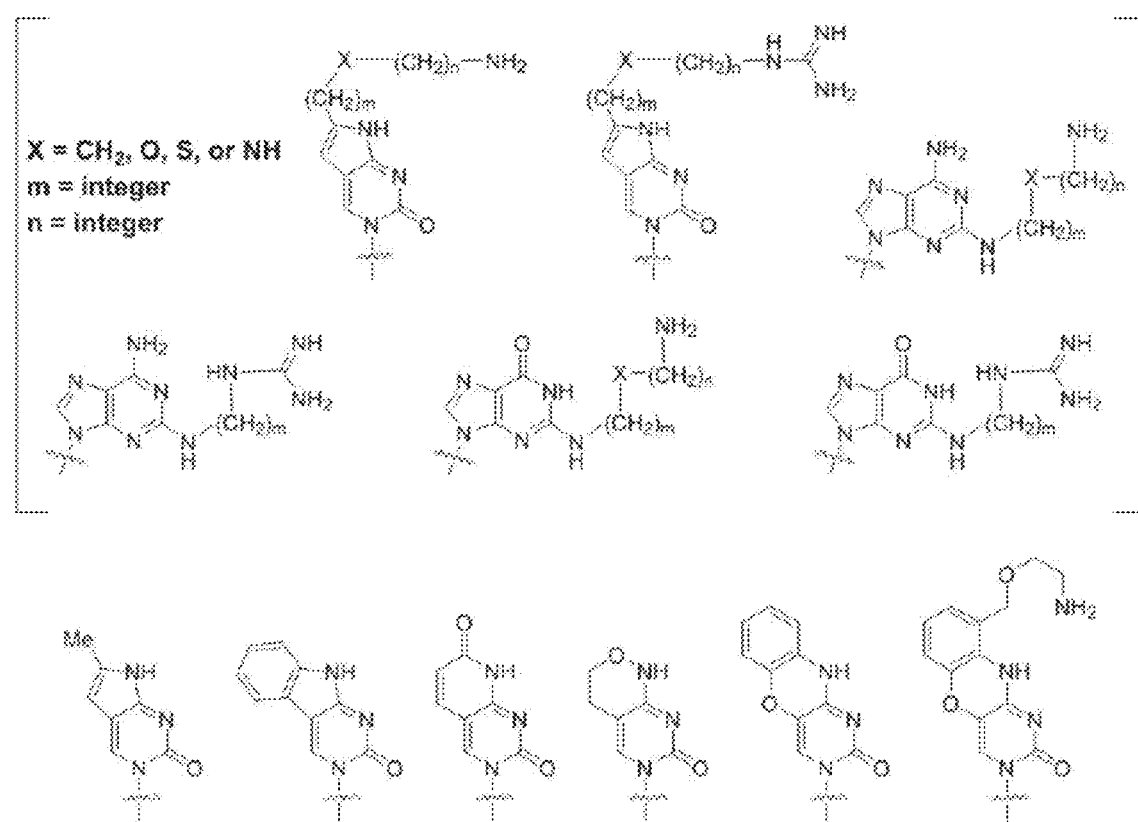
Figure 2A:
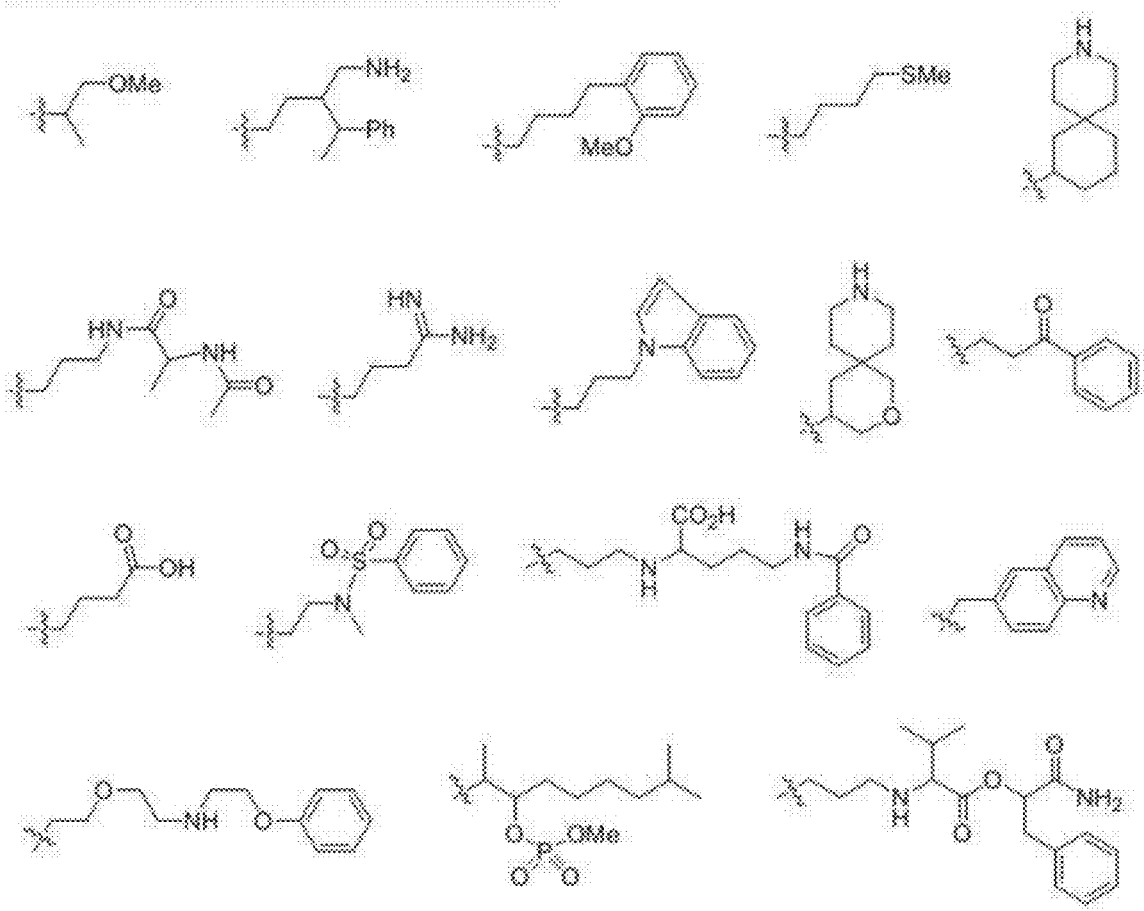
Figure 4:
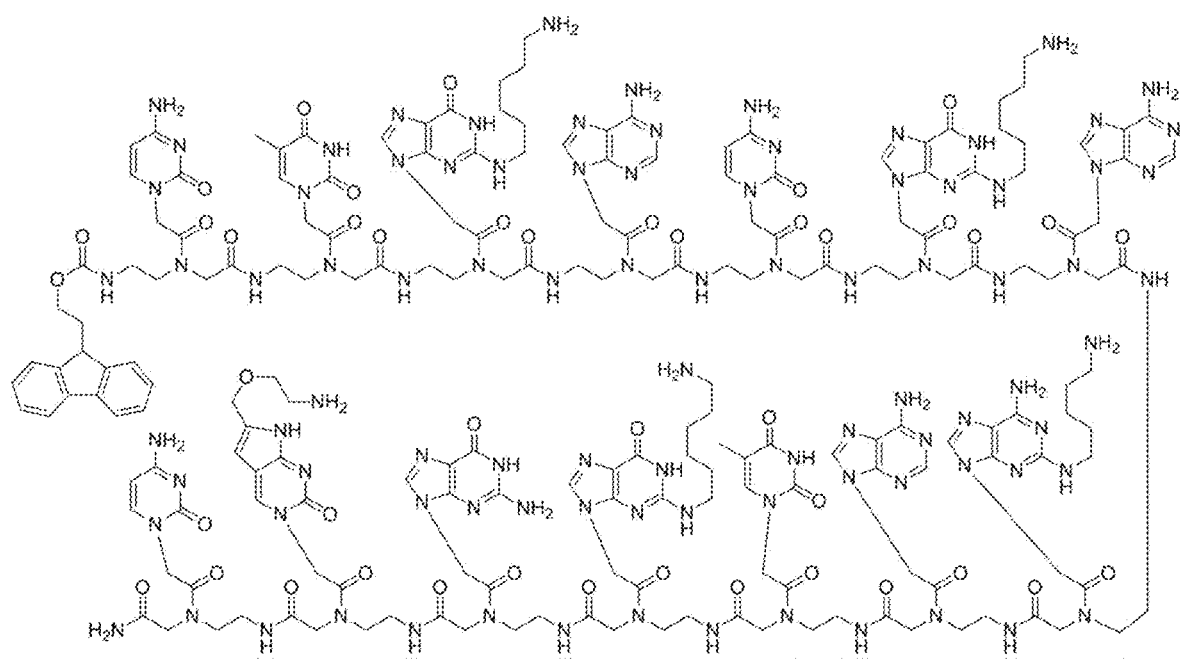
FIG. 4. Chemical structure of "ASO 1".
Figure 6A:
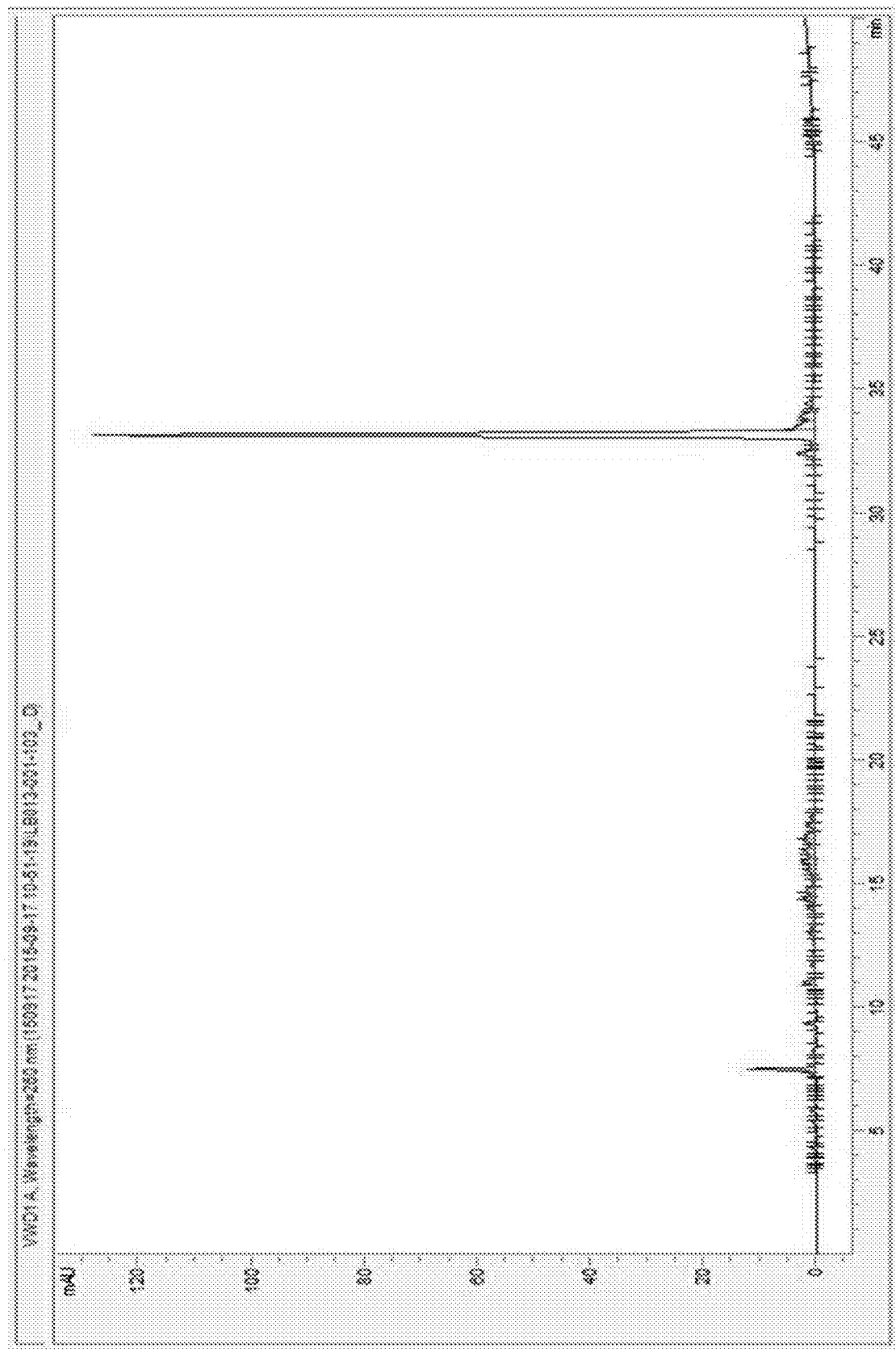
FIGS. 6a-6b. Cis-reverse phase HPLC chromatograms of "ASO 1" before and after HPLC purification, respectively.
Figure 6B:
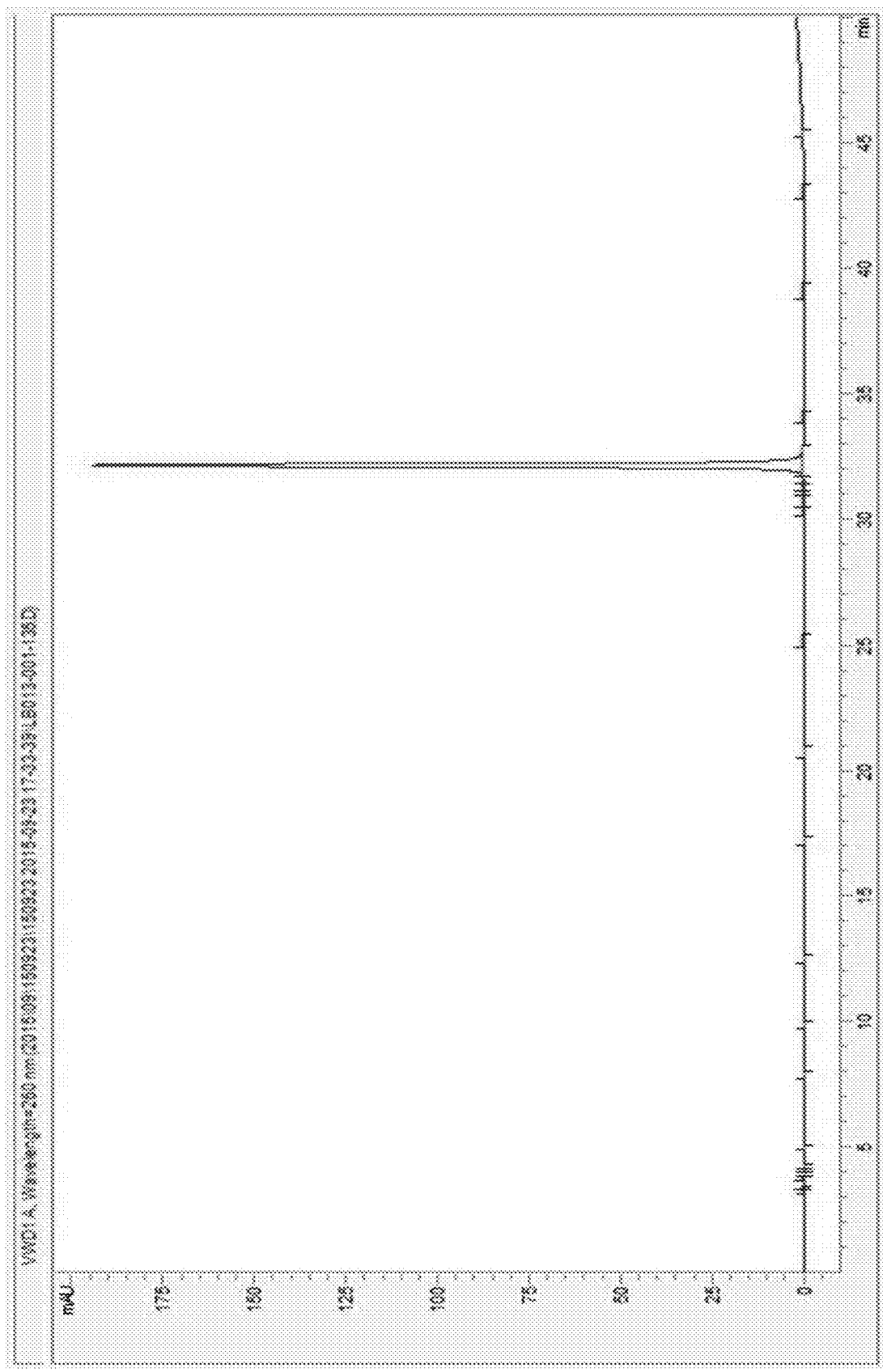
Figure 7:
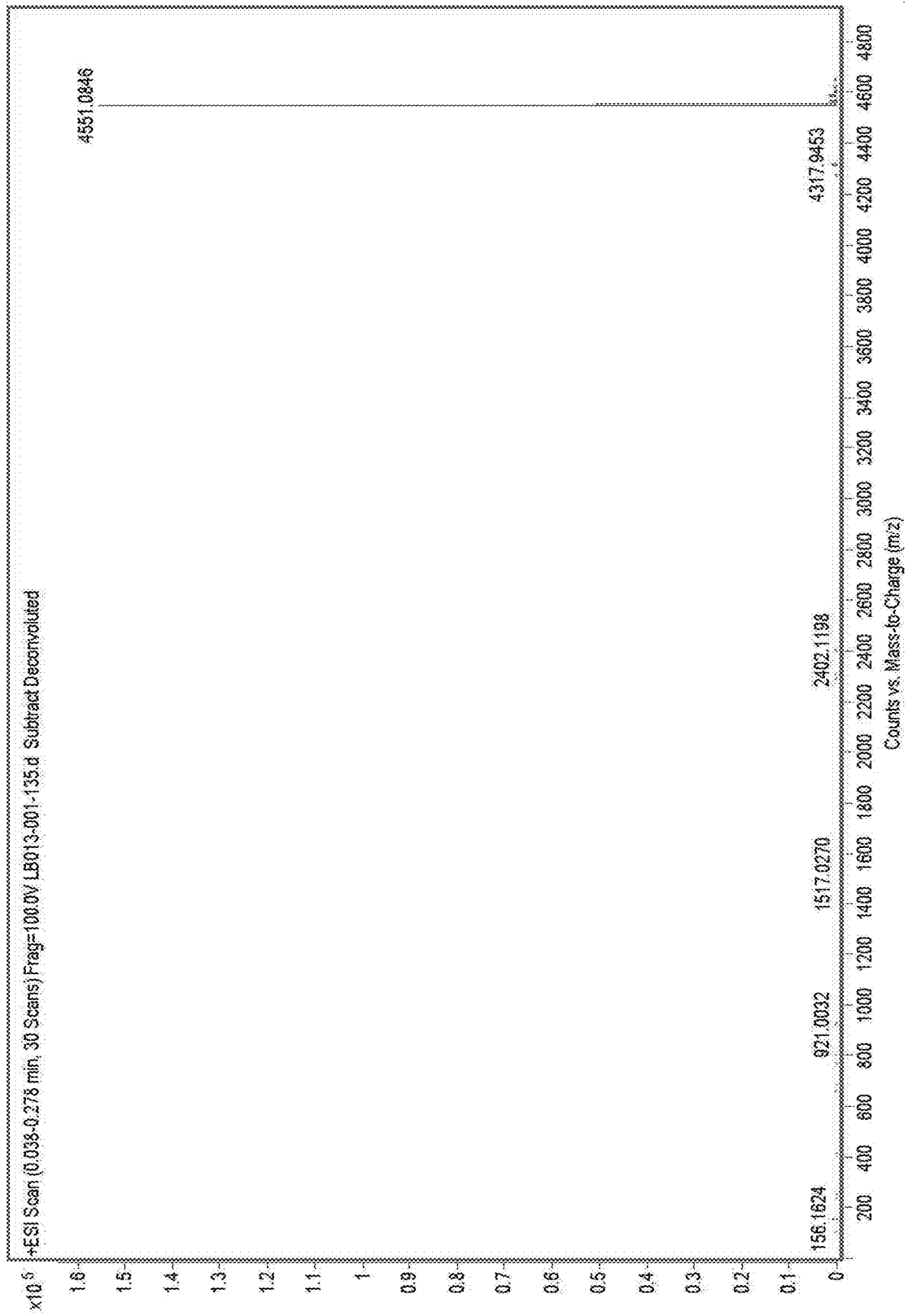
FIG. 7. ESI-TOF mass spectrum of "ASO 1" purified by $C_{18}$-RP prep HPLC.

[HPLC Analysis and Purification] Following a cleavage from resin, the crude product of a PNA derivative was purified by Cis-reverse phase HPLC eluting water/acetonitrile or water/methanol (gradient method) containing 0.1% TFA. FIGS. 6a and 6b are exemplary HPLC chromatograms for "ASO 1" before and after HPLC purification, respectively.

Synthetic Examples for PNA Derivative of Formula I

In order to complementarily target the 5' splice site of "exon 12" in the human ACC2 pre-mRNA, PNA derivatives of this invention were prepared according to the synthetic procedures provided above or with minor modifications. Provision of such PNA derivatives targeting the human ACC2 pre-mRNA is to exemplify the PNA derivatives of Formula I, and should not be interpreted to limit the scope of the present invention.

TABLE 1

PNA derivatives complementarily targeting the 5' splice site of "exon 12" in the human ACC2 pre-mRNA along with structural characterization data by mass spectrometry.

| PNA Example | PNA Sequence (N→C) | Exact Mass, m/z theor.[a] | obs.[b] |
|---|---|---|---|
| ASO 1 | Fethoc-CTG(6)—ACG(6)—AA(5)A—TG(6)G—C(1O2)C—NH₂ | 4549.07 | 4549.08 |
| ASO 2 | Fethoc-TA(5)C(1O2)—TGA(5)—CGA(5)—AA(5)T—G(6)GC(1O2)—C—NH₂ | 5289.43 | 5289.38 |
| ASO 3 | Fethoc-TA(5)C—TG(5)A-C(1O2)GA(5)—AA(5)T—G(5)G—NH₂ | 4661.14 | 4661.18 |
| ASO 4 | Fethoc-AC(1O2)T—GA(5)C-GA(5)A—A(5)TG(5)—GC(1O2)—NH₂ | 4658.11 | 4658.10 |
| ASO 5 | Fethoc-CTG(6)—AC(1O2)G—A(5)AA(5)—TG(6)G—NH₂ | 4047.86 | 4047.87 |
| ASO 6 | Fethoc-CTG(6)—AC(1O2)G—A(5)AA(5)—TG(6)G—C(1O2)C—NH₂ | 4647.12 | 4647.12 |

[a]theoretical exact mass,
[b]observed exact mass

Table 1 provides PNA derivatives complementarily targeting the 5' splice site of "exon 12" in the human ACC2 pre-mRNA read out from the human ACC2 gene [NCBI Reference Sequence: NG_046907] along with structural characterization data by mass spectrometry. Provision of the peptide nucleic acid derivatives of the present invention in Table 1 is to exemplify the PNA derivatives of Formula I, and should not be interpreted to limit the scope of the present invention.

"ASO 1" has a 14-mer complementary overlap with the 14-mer sequence marked "bold" and "underlined" within the 30-mer RNA sequence of [(5'→3') GGAAGAGGC-CAUUUC|gucaguaucuccuuc] (SEQ. NO. 8) spanning the junction of "exon 12" and "intron 12" in the human ACC2 pre-mRNA. Thus "ASO 1" possesses a 9-mer overlap with "exon 12" and a 5-mer overlap with "intron 12" within the human ACC2 pre-mRNA.

Binding Affinity of "ASO" for Complementary DNA

The PNA derivatives of Formula I were evaluated for their binding affinity for 10-mer DNAs complementarily targeting either the N-terminal or C-terminal. The binding affinity was assessed by $T_m$ value for the duplex between PNA and 10-mer complementary DNA. The duplex between PNA derivatives and fully complementary DNAs show $T_m$ values too high to be reliably determined in aqueous buffer solution, since the buffer solution tends to boil during the $T_m$ measurement. $T_m$ values for full length PNAs can be predicted and compared based on the $T_m$ value for the duplex between PNA and 10-mer complementary DNA.

$T_m$ values were determined on a UV/Vis spectrometer as follows. A mixed solution of 4 M PNA oligomer and 4 μM complementary 10-mer DNA in 4 mL aqueous buffer (pH 7.16, 10 mM sodium phosphate, 100 mM NaCl) in 15 mL polypropylene falcon tube was incubated at 90° C. for a few minute and slowly cooled down to ambient temperature. Then the solution was transferred into a 3 mL quartz UV cuvette equipped with an air-tight cap, and the cuvette was mounted on an Agilent 8453 UV/Visible spectrophotometer. The absorbance changes at 260 nm were recorded with increasing the temperature of the cuvette by either 0.5 or 1° C. per minute. From the absorbance vs temperature curve, the temperature showing the largest increase rate in absorbance was read out as the $T_m$ between PNA and 10-mer DNA. The DNAs for $T_m$ measurement were purchased from Bioneer (www.bioneer.com, Dajeon, Republic of Korea) and used without further purification.

Observed $T_m$ values of the PNA derivatives of Formula I are very high for a complementary binding to 10-mer DNA as provided in Table 2.

TABLE 2

$T_m$ values between PNAs and 10-mer complementary DNA targeting either the N-terminal or the C-terminal of PNA.

| | $T_m$ Value, ° C. | |
|---|---|---|
| PNA | 10-mer DNA against N-Terminal | 10-mer DNA against C-Terminal |
| ASO 1 | 72.80 | 79.60 |
| ASO 2 | 82.99 | 82.01 |
| ASO 3 | 76.03 | 78.99 |
| ASO 4 | 80.01 | 82.01 |

For example, "ASO 1" showed a $T_m$ value of 72.80° C. for the duplex with the 10-mer complementary DNA targeting the N-terminal 10-mer in the PNA as marked "bold" and "underlined" in [(N→C) Fethoc-CTG(6)-ACG(6)-AA(5)A-TG(6)G-C(1O2)C—NH₂] (SEQ. NO. 1). In the meantime, "ASO 1" showed a $T_m$ of 79.60° C. for the duplex with the 10-mer complementary DNA targeting the C-terminal 10-mer in the PNA as marked "bold" and "underlined" in [(N→C) Fethoc-CTG(6)-ACG(6)-AA(5)A-TG(6)G-C(1O2)C—NH₂] (SEQ. NO. 1).

Examples for Biological Activities of PNA Derivatives of Formula I

PNA derivatives in this invention were evaluated for in vitro ACC2 antisense activities in C2C12 skeletal muscle cells by use of real-time quantitative polymerase chain reaction (RT-qPCR) and so on. The biological examples were provided as examples to illustrate the biological profiles of the PNA derivatives of Formula I, and therefore should not be interpreted to limit the scope of the current invention.

Example 1. Exon Skipping Induced by "ASO 1" in C2C12

"ASO 1" was evaluated for its ability to induce the skipping of ACC2 "exon 12" in C2C12 cells as described below.

[Cell Culture & ASO Treatment] C2C12 cells (2×10⁵) (Cat. No. CRL-1772, ATCC) were grown in 60 mm culture dish containing DMEM medium (Dulbecco Modified Eagle Medium: DMEM) (Cat. No. 12-604F, Lonza) supplemented with 10% FBS (Fetal Bovine Serum) (Cat. No. 10099-41, GIBCO) and 1% streptomycin/penicillin (Cat. No. 15140-122, GIBCO) under 5% $CO_2$ atmosphere at 37° C. The cells were treated either with nothing (negative control) or with an aliquot of aqueous stock solution of "ASO 1" for 5 hours at 100 zM to 1 fM.

[RNA Extraction & Nested PCR] Total RNA was extracted using RNeasy Mini kit (Qiagen, Cat. No. 714106) according to the manufacturer's instructions from "ASO 1" treated cells and cDNA was prepared from 200 ng of RNA by use of SuperScript™ III One-Step RT-PCR System (Cat. No. 12574-018, Invitrogen). To a mixture of 200 ng of RNA, 25 microliter of 2× Reaction Mix buffer, 2 microliter of SuperScript III™ RT/Platinum Taq Mix, 1 microliter of 10 M (micromole conc.) Exon 9 Forward Primer (5'-TTTTCCGACAAGTGCAGAG-3') (SEQ. NO. 9), and 1 microliter of 10 Mm Exon 15 Reverse Primer (5'-AACGTC-CACAATGTTCAG-3') (SEQ. NO. 10) in PCR tube was added autoclaved distilled water to a total volume of 50 microliter. After reaction at 60° C. for 30 minutes and at 94° C. for 2 minutes, 30 cycles PCR process at 94° C. for 15 seconds, at 50° C. for 30 seconds, and at 68° C. for 1 minute afforded the first crude product. The mixture of 1 microliter of the crude product, 1 microliter of 10 μM Exon 10 Forward Primer (5'-GAG TAC TTA TAC AGC CAG G-3') (SEQ. NO. 11), and 1 microliter of 10 μM Exon 14 Reverse Primer (5'-TTC TGA ACA TCG CGT CTG-3') (SEQ. NO. 12) was reacted, using PyroHostStart Taq Polymerase Kit (Cat. No. K-2611-FCG) according to the manufacturer's instructions, at 95° C. for 2 minutes, and then was under PCR process at 95° C. for 30 seconds, at 47° C. for 1 minute, and at 72° C. for 20 seconds.

[Identification of Exon Skipping Products Electrophoresis] The PCR products (10 microliter) were subjected to electrophoretic separation on a 2% agarose gel. The target bands from "ASO 1" treatment were collected and analyzed by Sanger Sequencing to evaluate exon skipping sequence.

Figure 8:
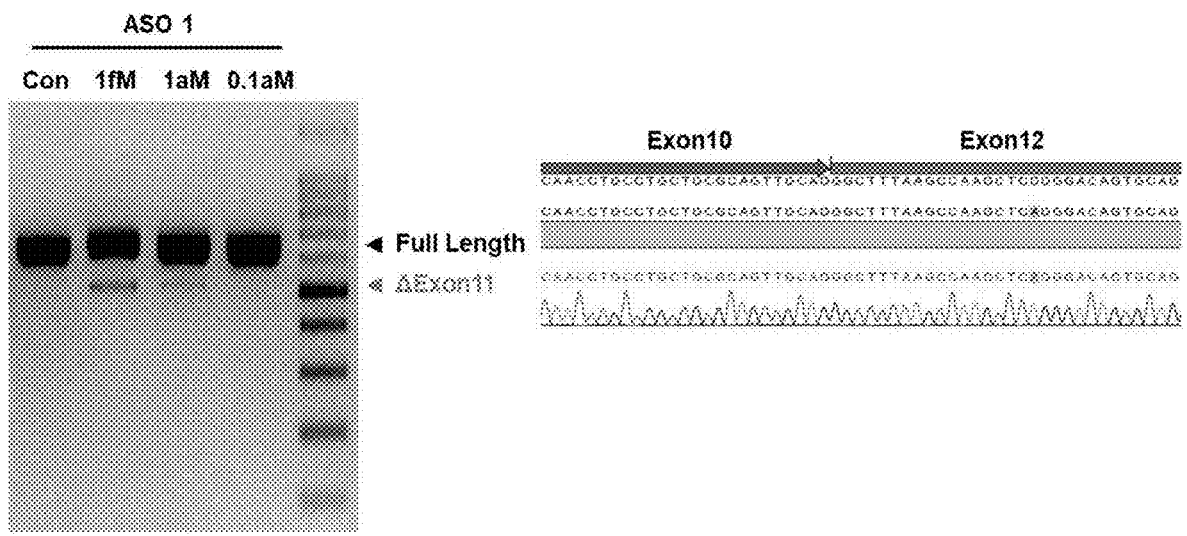
FIG. 8. Exon Skipping of ACC2 mRNA by "ASO 1" in C2C12.

[Exon Skipping Induced by "ASO 1"] As can be seen in FIG. 8, the cells treated with "ASO 1" at 0.1 aM to 1 fM concentration-dependently yielded the splice variant ACC2 mRNA lacking exon 11.

Example 2. Inhibition of ACC2 mRNA Formation by "ASO 1" in C2C12

"ASO 1" was evaluated by Real-Time qPCR for its ability to down-regulate the ACC2 mRNA formation in C2C12 as described below.

[Cell Culture & ASO Treatment] C2C12 cells (Cat. No. CRL-1772, ATCC) were maintained in Dulbecco Modified Eagle Medium (DMEM, Cat. No. 12-604F, Lonza) supplemented with 10% Fetal Bovine Serum (Cat. No. 10099-41, GIBCO) and 1% streptomycin/penicillin (Cat. No. 15140-122, GIBCO), which was grown at 37° C. and under 5% $CO_2$ condition. C2C12 cells ($2\times10^5$) stabilized for 24 hours in 60 mm culture dish were incubated for 24 hours with "ASO 1" at 0 (negative control) and 100 zM to 1 fM.

[RNA Extraction & cDNA Synthesis] Total RNA was extracted using RNeasy Mini kit (Qiagen, Cat. No. 714106) according to the manufacturer's instructions from "ASO 1" treated cells and cDNA was prepared from 400 ng of RNA by use of PrimeScript™ 1st strand cDNA Synthesis Kit (Takara, Cat. No. 6110A). To a mixture of 400 ng of RNA, 1 microliter of random hexamer, and 1 microliter of dNTP (10 mM) in PCR tube was added DEPC-treated water to a total volume of 10 microliter, which was reacted at 65° C. for 5 minutes. cDNA was synthesized by adding 10 microliter of PrimeScript RTase to the reaction mixture and reacting at 30° C. for 10 minutes and at 42° C. for 60 minutes, successively.

[Quantitative Real-Time PCR] In order to evaluate the expression level of human ACC2 mRNA real-time qPCR was performed with synthesized cDNA by use of Taqman probe. The mixture of cDNA, Taqman probe (Thermo, Mm01204651), IQ supermix (BioRad, Cat. No. 170-8862), and nuclease free water in PCR tube was under reaction by use of CFX96 Touch Real-Time system (BioRad) according to the cycle conditions specified as follows: at 95° C. for 3 min (primary denaturation) followed by 50 cycles of 10 sec at 95° C. (denaturation) and 30 sec at 60° C. (annealing and polymerization). Fluorescence intensity was measured at the end of every cycle and the result of PCR was evaluated by the melting curve. After the threshold cycle (Ct) of each gene was standardized by that of GAPDH, the change of Ct was compared and analyzed.

Figure 9:
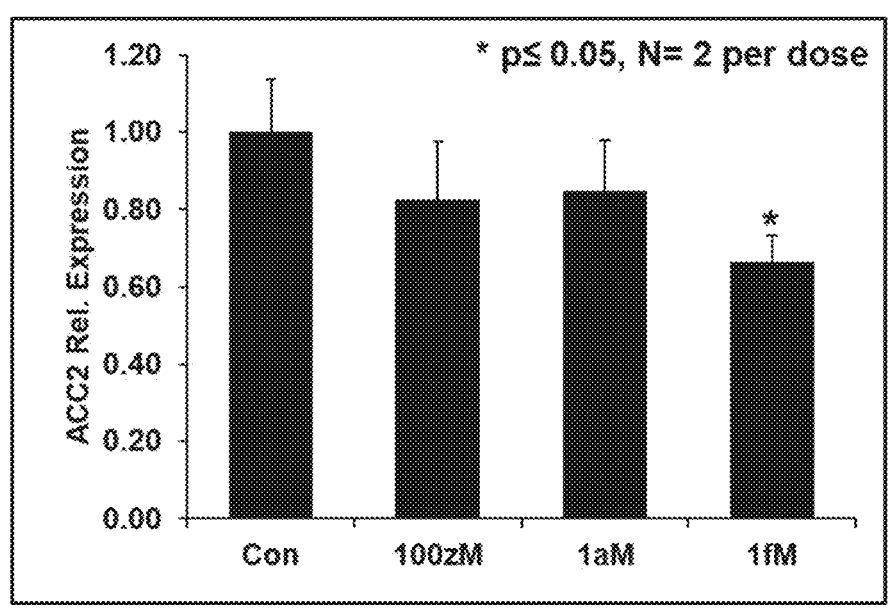
FIG. 9. Inhibition of ACC2 mRNA Levels by "ASO 1" in C2C12.

[ACC2 mRNA Decrease by "ASO 1"] As can be seen in FIG. 9, compared to control experiment the amount of ACC2 mRNA was reduced at 100 zM to 1 fM treatment of "ASO 1", concentration-dependently, and statistically significant 30% of reduction was observed at 1 fM treatment of "ASO 1". (Student T-test was done to check the statistical significance of the findings)

Example 3. Inhibition of ACC2 mRNA Formation by "ASO 6" in C2C12

"ASO 6" was evaluated by Real-Time qPCR for its ability to down-regulate the ACC2 mRNA formation in C2C12 as described below.

[Cell Culture & ASO Treatment] C2C12 cells (Cat. No. CRL-1772, ATCC) were maintained in Dulbecco Modified Eagle Medium (DMEM, Cat. No. 12-604F, Lonza) supplemented with 10% Fetal Bovine Serum (Cat. No. 10099-41, GIBCO) and 1% streptomycin/penicillin (Cat. No. 15140-122, GIBCO), which was grown at 37° C. and under 5% $CO_2$ condition. C2C12 cells ($2\times10^5$) stabilized for 24 hours in 60 mm culture dish were incubated for 24 hours with "ASO 6" at 0 (negative control) and 100 zM to 1 fM.

[RNA Extraction & cDNA Synthesis] Total RNA was extracted using RNeasy Mini kit (Qiagen, Cat. No. 714106) according to the manufacturer's instructions from "ASO 6" treated cells and cDNA was prepared from 400 ng of RNA by use of PrimeScript™ 1st strand cDNA Synthesis Kit (Takara, Cat. No. 6110A). To a mixture of 400 ng of RNA, 1 microliter of random hexamer, and 1 microliter of dNTP (10 mM) in PCR tube was added DEPC-treated water to a total volume of 10 microliter, which was reacted at 65° C. for 5 minutes. cDNA was synthesized by adding 10 microliter of PrimeScript RTase to the reaction mixture and reacting at 30° C. for 10 minutes and at 42° C. for 60 minutes, successively.

[Quantitative Real-Time PCR] In order to evaluate the expression level of human ACC2 mRNA real-time qPCR was performed with synthesized cDNA by use of Taqman probe. The mixture of cDNA, Taqman probe (Thermo, Mm01204651), IQ supermix (BioRad, Cat. No. 170-8862), and nuclease free water in PCR tube was under reaction by use of CFX96 Touch Real-Time system (BioRad) according to the cycle conditions specified as follows: at 95° C. for 3 min (primary denaturation) followed by 50 cycles of 10 sec at 95° C. (denaturation) and 30 sec at 60° C. (annealing and polymerization). Fluorescence intensity was measured at the end of every cycle and the result of PCR was evaluated by the melting curve. After the threshold cycle (Ct) of each gene was standardized by that of GAPDH, the change of Ct was compared and analyzed.

Figure 10:
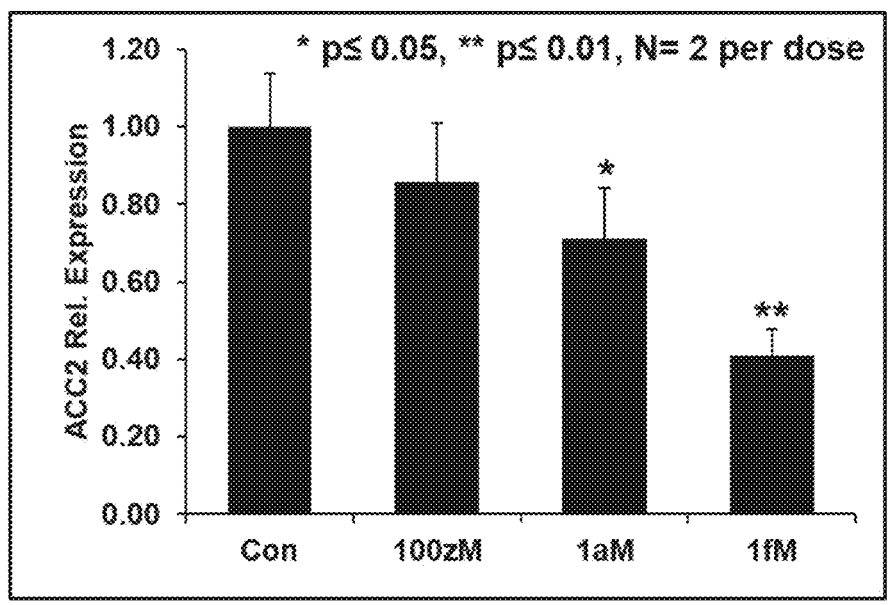
FIG. 10. Inhibition of ACC2 mRNA Levels by "ASO 6" in C2C12.

[ACC2 mRNA Decrease by "ASO 6"] As can be seen in FIG. 10, the amount of ACC2 mRNA was reduced at 100 zM to 1 fM treatment of "ASO 6", concentration-dependently. Compared to the control experiment, statistically significant 30% and 50% reduction was observed at 1 aM and 1 fM treatment of "ASO 6", respectively. (Student T-test was done to check the statistical significance of the findings)

Example 4. Inhibition of ACC2 mRNA Formation by "ASO 5" in C2C12

"ASO 5" was evaluated by the same method as described below.

[Cell Culture & ASO Treatment] C2C12 cells (Cat. No. CRL-1772, ATCC) were maintained in Dulbecco Modified Eagle Medium (DMEM, Cat. No. 12-604F, Lonza) supplemented with 10% Fetal Bovine Serum (Cat. No. 10099-41, GIBCO) and 1% streptomycin/penicillin (Cat. No. 15140-122, GIBCO), which was grown at 37° C. and under 5% $CO_2$ condition. C2C12 cells ($2\times10^5$) stabilized for 24 hours in 60 mm culture dish were incubated for 24 hours with "ASO 5" at 0 (negative control) and 100 zM to 1 fM.

[RNA Extraction & cDNA Synthesis] Total RNA was extracted using RNeasy Mini kit (Qiagen, Cat. No. 714106) according to the manufacturer's instructions from "ASO 5" treated cells and cDNA was prepared from 400 ng of RNA by use of PrimeScript™ 1st strand cDNA Synthesis Kit (Takara, Cat. No. 6110A). To a mixture of 400 ng of RNA, 1 microliter of random hexamer, and 1 microliter of dNTP (10 mM) in PCR tube was added DEPC-treated water to a total volume of 10 microliter, which was reacted at 65° C. for 5 minutes. cDNA was synthesized by adding 10 microliter of PrimeScript RTase to the reaction mixture and reacting at 30° C. for 10 minutes and at 42° C. for 60 minutes, successively.

[Quantitative Real-Time PCR] In order to evaluate the expression level of human ACC2 mRNA real-time qPCR was performed with synthesized cDNA by use of Tagman probe. The mixture of cDNA, Taqman probe (Thermo, Mm01204651), IQ supermix (BioRad, Cat. No. 170-8862), and nuclease free water in PCR tube was under reaction by use of CFX96 Touch Real-Time system (BioRad) according to the cycle conditions specified as follows: at 95° C. for 3 min (primary denaturation) followed by 50 cycles of 10 sec at 95° C. (denaturation) and 30 sec at 60° C. (annealing and polymerization). Fluorescence intensity was measured at the end of every cycle and the result of PCR was evaluated by the melting curve. After the threshold cycle (Ct) of each gene was standardized by that of GAPDH, the change of Ct was compared and analyzed.

Figure 11:
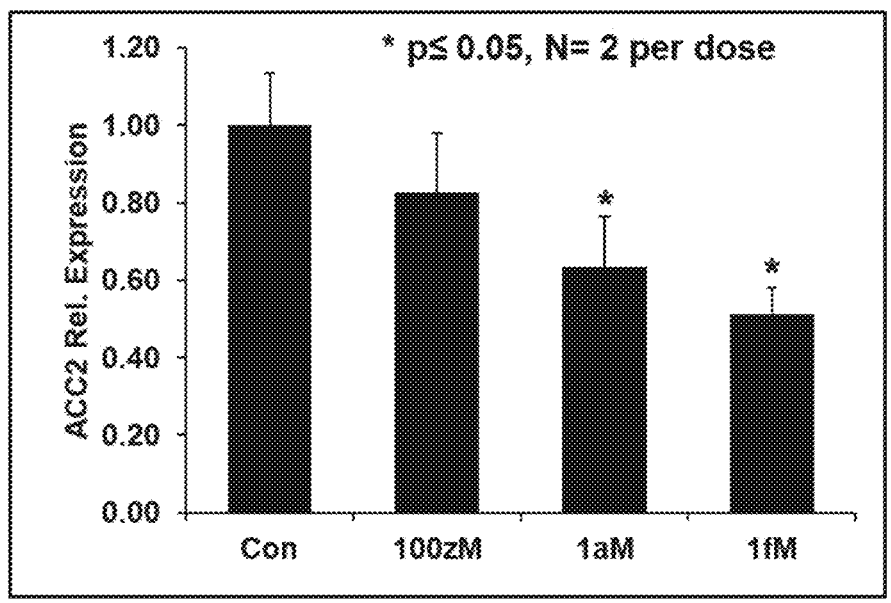
FIG. 11. Inhibition of ACC2 mRNA Levels by "ASO 5" in C2C12.
Figure 12:
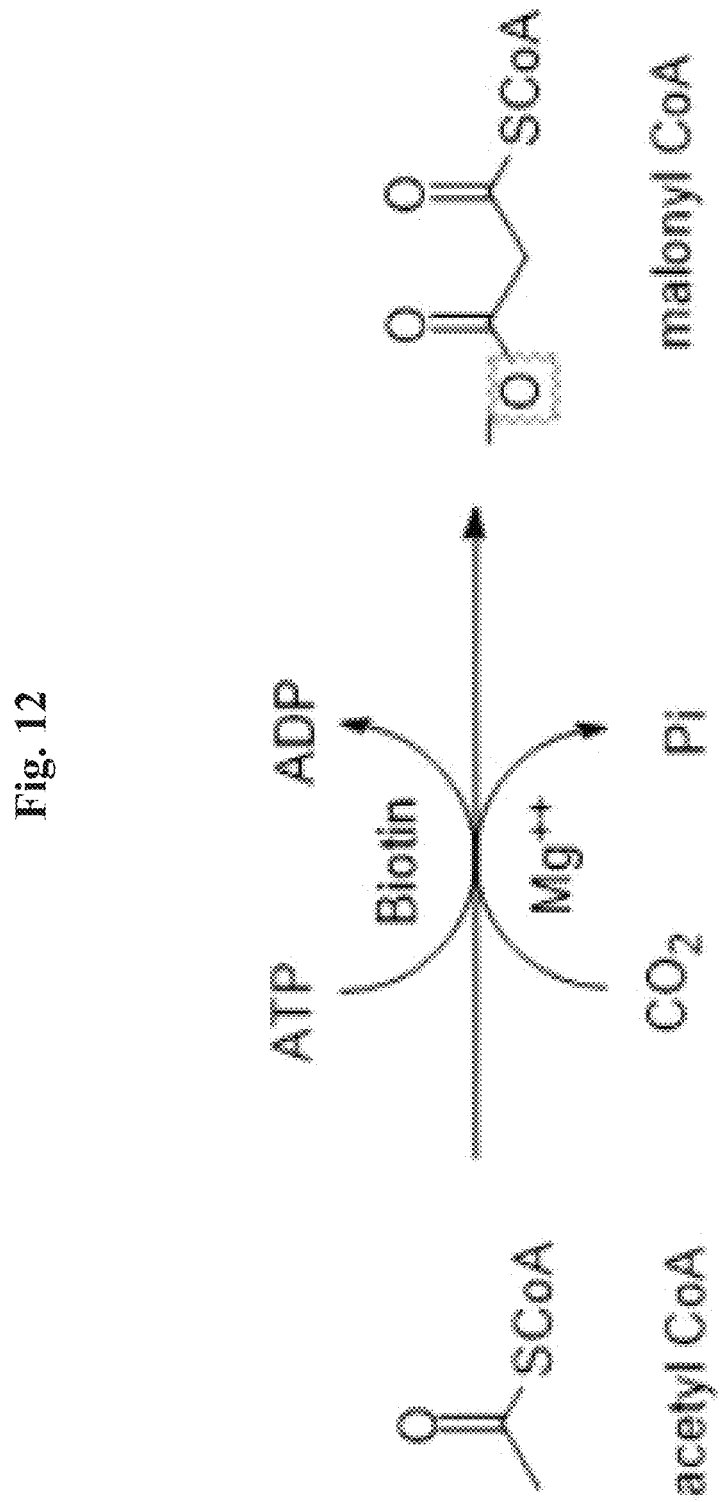
FIG. 12. Production of malonyl-CoA through Acetyl-CoA carboxylase (ACC) catalyzing the carboxylation of acetyl-CoA.
Figure 13:
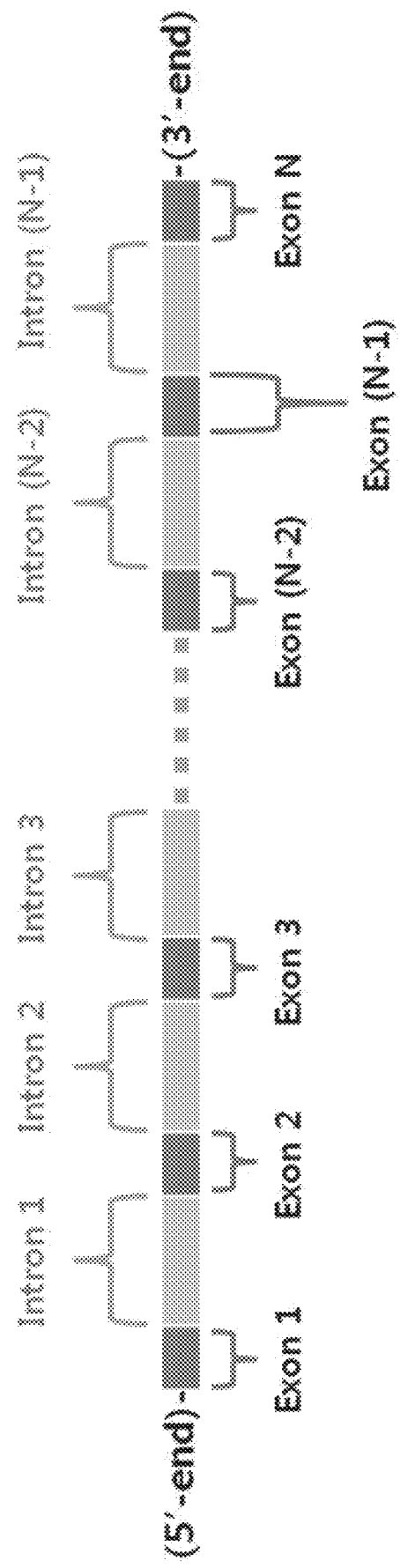
FIG. 13. An exemplified numbered exons and introns.
Figure 14:
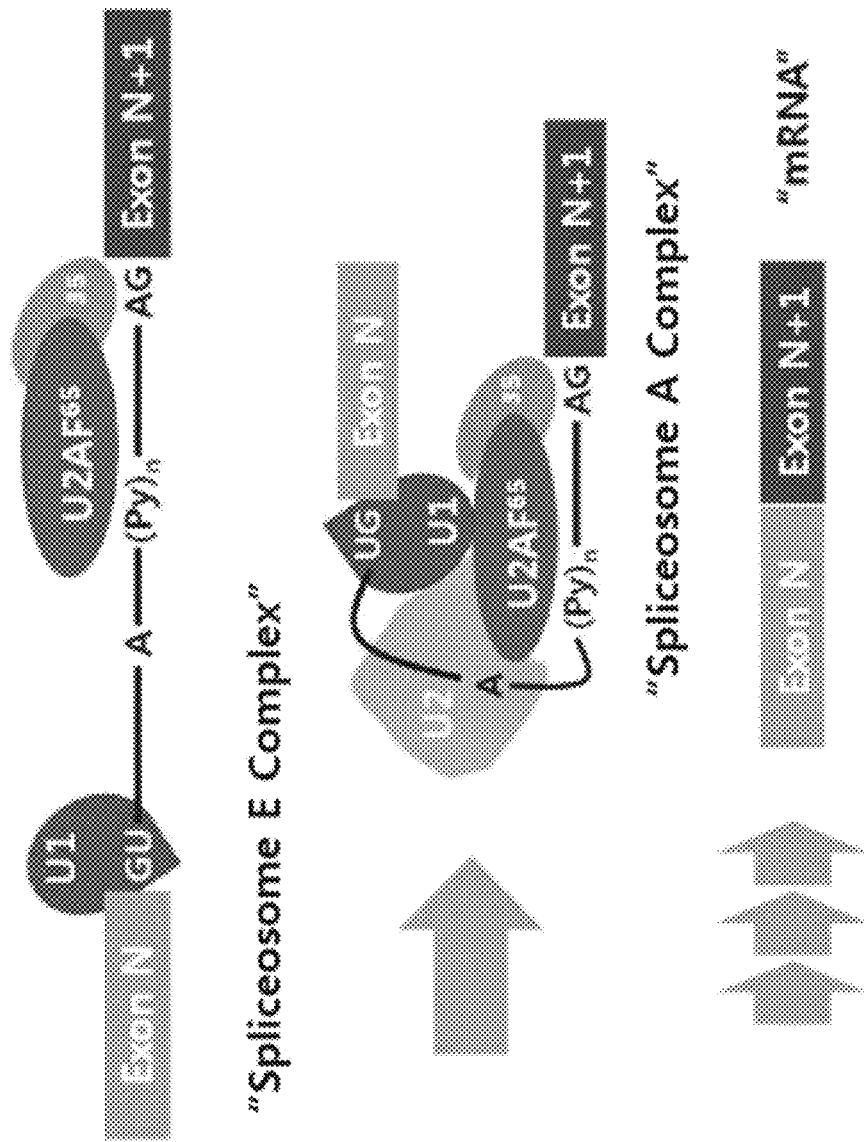
FIG. 14. A schematic summary of Pre-mRNA processed into mRNA by "splicing".
Figure 15:
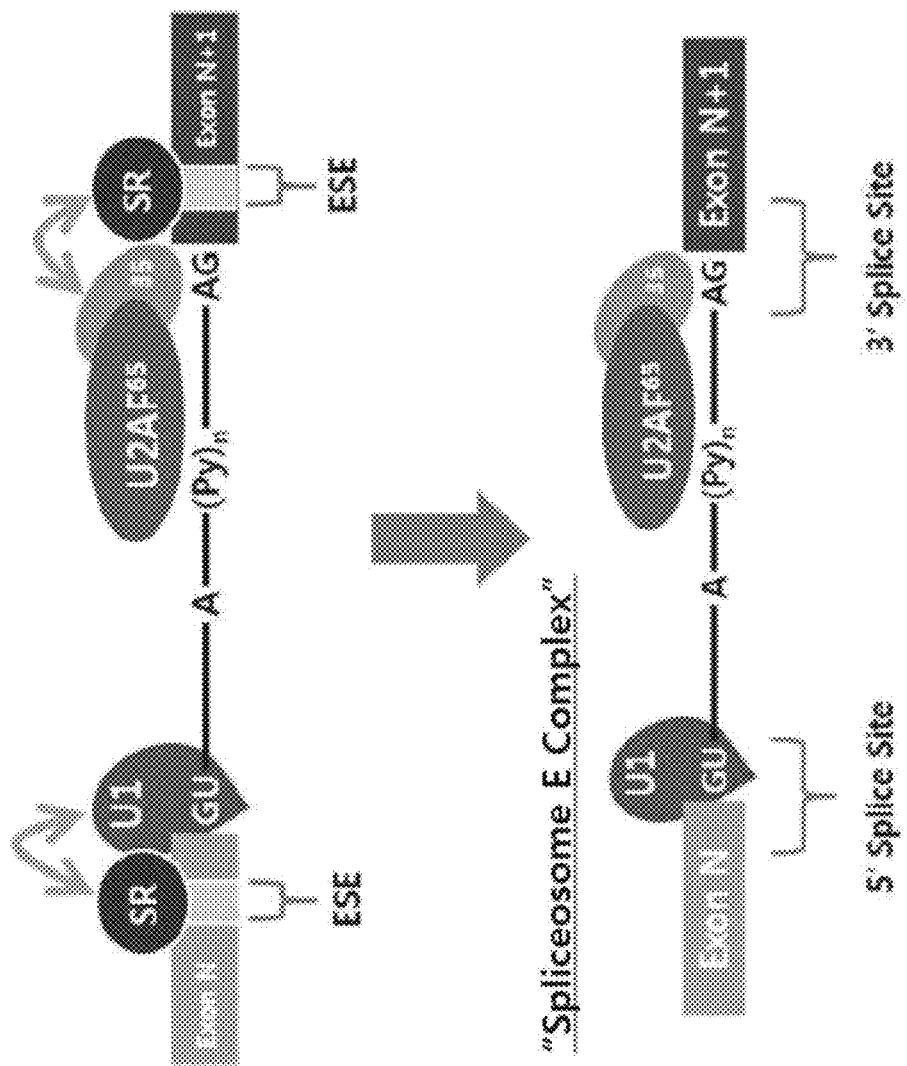
FIG. 15. A scheme illustrating 3' splice site and 5' splice site.

[ACC2 mRNA Decrease by "ASO 5"] As can be seen in FIG. 11, the amount of ACC2 mRNA was reduced at 100 zM to 1 fM treatment of "ASO 5", concentration-dependently. Compared to the control experiment, statistically significant 30% and 42% reduction was observed at 1 aM and 1 fM treatment of "ASO 5", respectively. (Student T-test was done to check the statistical significance of the findings)

Example 5. Preparation of Body Lotion Containing Compound of Formula I. (w/w %)

A compound of Formula I, for example "ASO 1" was formulated as a body lotion for topical application to subjects. The body lotion was prepared as described below. Given that there are lots of variations of body lotion possible, this preparation should be taken as an example and should not be interpreted to limit the scope of the current invention.

In a separate beaker, mixed substances of part A and part B were dissolved at 80° C., respectively. Part A and part B was mixed and emulsified by use of 3,600 rpm homogenizer at 80° C. for 5 minutes. Emulsified part C was filtered through 50 mesh and the filtrate was added to the mixture of part A and B. The resulting mixture was emulsified by use of 3,600 rpm homogenizer at 80° C. for 5 minutes. After addition of part D to the mixture of part A, B, and C at 35° C., the resulting mixture was emulsified by use of 2,500 rpm homogenizer at 25° C. for 3 minutes. Finally make sure homogeneous dispersion and complete defoamation.

TABLE 3

Example of Composition for Body Lotion Containing Compound of Formula I. (w/w %)

| Part | No. | Substance Name | Amount |
|---|---|---|---|
| A | 1 | Polyglyceryl-3 Methylglucose Distearate | 0.700 |
|  | 2 | Glyceryl Stearate | 0.300 |
|  | 3 | Cetearyl Alcohol | 1.000 |
|  | 4 | Shea Butter | 1.000 |
|  | 5 | Caprylic/Capric Triglyceride | 3.000 |
|  | 6 | Dicaprylyl Carbonate | 4.000 |
|  | 7 | Dimethicone | 0.500 |
|  | 8 | Ethylhexylglycerin | 0.300 |
| B | 9 | Glycerin | 5.000 |
|  | 10 | Propanediol | 5.000 |
|  | 11 | 1,2-Hexanediol | 0.300 |
|  | 12 | Arginine | 0.160 |
|  | 13 | Deionized Water | 62.110 |
| C | 14 | Sodium Acrylate/Sodium Acryloyldimethyl Tau Copolymer | 0.300 |
|  | 15 | Carbomer | 0.200 |
|  | 16 | Xanthan Gum | 0.030 |
|  | 17 | Deionized Water | 13.000 |
| D | 18 | Perfume | 0.100 |
|  | 19 | Oligomer [1000 fM] + POLYSORBATE 80 [0.1%] | 3.000 |
|  |  | SUM | 100.000 |

Example 6. Preparation of Face Cream Containing Compound of Formula I. (w/w %)

A compound of Formula I, for example "ASO 1" was formulated as a face cream for topical application to subjects. The face cream was prepared as described below. Given that there are lots of variations of topical cream possible, this preparation should be taken as an example and should not be interpreted to limit the scope of the current invention.

TABLE 4

Example of Composition for Face Cream Containing Compound of Formula I. (w/w %)

| Part | No. | Substance Name | Amount (%/%) |
|---|---|---|---|
| A | 1 | Caprylic/Capric Triglyceride | 2.000 |
|   | 2 | Glyceryl Stearate/Polyglyceryl-10 Stearate | 10.000 |
|   | 3 | Cetearyl Alcohol | 2.000 |
|   | 4 | Ethylhexylglycerin | 0.300 |
| B | 10 | Glycerin | 5.000 |
|   | 11 | 1,2-Hexanediol | 0.300 |
|   | 12 | Deionized Water | 78.900 |
| C | 14 | Hydroxyethyl Acrylate/Sodium Acryloyldimethyl Tau Copolymer | 1.000 |
| D | 19 | Oligomer [1000 fM] + POLYSORBATE 80 [0.1%] | 0.500 |
|   |   | SUM | 100.000 |

In a separate beaker, mixed substances of part A and part B were dissolved at 80° C., respectively. Part A and part B was mixed and emulsified by use of 3,600 rpm homogenizer at 80° C. for 5 minutes. After addition of part C to the mixture of part A and B, the resulting mixture was emulsified by use of 3,600 rpm homogenizer at 80° C. for 5 minutes. After addition of part D to the mixture of part A, B, and C at 35° C., the resulting mixture was emulsified by use of 3,600 rpm homogenizer at 35° C. for 5 minutes. Finally make sure homogeneous dispersion and complete defoamation at 25° C.

The invention claimed is:

1. A peptide nucleic acid derivative represented by Formula I, or a pharmaceutically acceptable salt thereof, for inducing exon skipping within human ACC2 pre-mRNA:

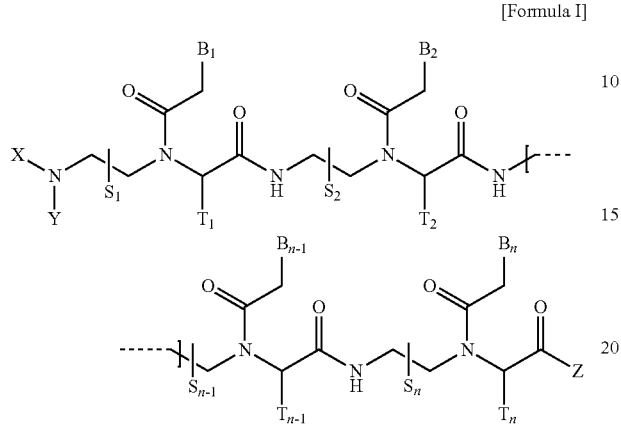

[Formula I]

wherein, n is an integer between 11 and 15;

the compound of Formula I possesses at least a 10-mer complementary overlap with the 18-mer pre-mRNA sequence of [(5'-3') GGCCAUUUCGUCAGUAUC] (SEQ ID NO: 7) in the human ACC2 pre-mRNA;

the compound of Formula I is fully complementary to the human ACC2 pre-mRNA, or partially complementary to the human ACC2 pre-mRNA with one or two mismatches;

$S_1, S_2, \ldots, S_{n-1}, S_n, T_1, T_2, \ldots, T_{n-1}$, and $T_n$ are hydrido radical;

X and Y independently represent hydrido, or substituted or non-substituted alkyloxycarbonyl radical;

Z represents substituted or non-substituted amino radical; and $B_1, B_2, \ldots, B_{n-1}$, and $B_n$ are independently selected from natural nucleobases including adenine, thymine, guanine, cytosine and uracil, and unnatural nucleobases; and, at least four of $B_1, B_2, \ldots, B_{n-1}$, and $B_n$ are independently selected from unnatural nucleobases represented by Formula II, Formula III, or Formula IV

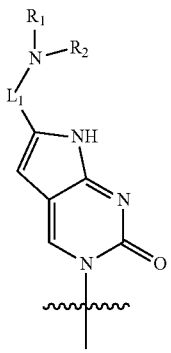

[Formula II]

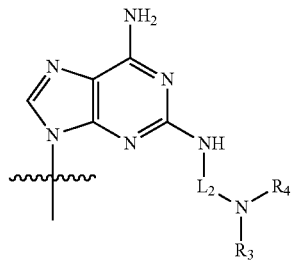

[Formula III]

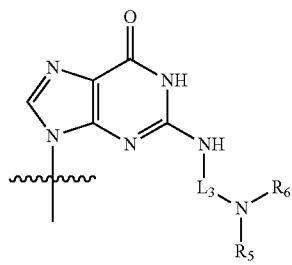

[Formula IV]

wherein, $R_1, R_2, R_3, R_4, R_5$ and $R_6$ are hydrido radical;

L1 represents —(CH$_2$)$_2$—O—(CH$_2$)$_2$—, —CH$_2$—O—(CH$_2$)$_2$—, —CH$_2$—O—(CH$_2$)$_3$—, —CH$_2$—O—(CH$_2$)$_4$—, or —CH$_2$—O—(CH$_2$)$_5$—; and, L2 and L3 are independently selected from —(CH$_2$)$_2$—O—(CH$_2$)$_2$—, —(CH$_2$)$_3$—O—(CH$_2$)$_2$—, —(CH$_2$)$_2$—O—(CH$_2$)$_3$—, —(CH$_2$)$_2$—, —(CH$_2$)$_3$—, —(CH$_2$)$_4$—, —(CH$_2$)$_5$—, —(CH$_2$)$_6$—, —(CH$_2$)r, and —(CH$_2$)$_8$—.

2. The peptide nucleic acid derivative according to claim 1, which is selected from the group of peptide nucleic acid derivatives provided below, or a pharmaceutically acceptable salt thereof:

(N→C)   Fethoc-CTG(6)-ACG(6)-AA(5)A-TG(6)G-C(1O2)C—NH$_2$ [SEQ ID NO: 1];

(N→C)   Fethoc-CTG(6)-AC(1O2)G-A(5)AA(5)-TG(6)G-N H$_2$ [SEQ ID NO: 5];

and (N→C) Fethoc-CTG(6)-AC(1O2)G-A(5)AA(5)-TG(6)G-C(1O2)C—NH$_2$ [SEQ ID NO: 6]

wherein,

A, G, T, and C are monomers of peptide nucleic acid with a natural nucleobase of adenine, thymine, guanine and cytosine, respectively;

C(1O2), A(5), and G(6) are monomers of peptide nucleic acid with an unnatural nucleobase as follows:

C(1O2)

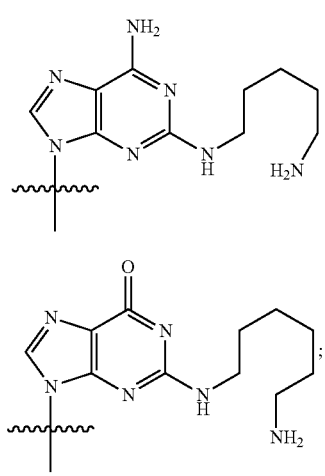

"Fethoc-" is the abbreviation for "[2-(9-fluorenyl)ethyl-1-oxy]carbonyl".

3. A method of inducing skipping of exon 12 in the human ACC2 pre-mRNA to yield a ACC2 mRNA splice variant lacking ACC2 exon 12 in cells in vitro, comprising contacting the cells with the peptide nucleic acid derivative according to claim 1, or a pharmaceutically acceptable salt thereof.

4. A cosmetic composition for improving conditions or disorders associated directly with human ACC2 gene transcription through downregulation of the ACC2 gene transcription, comprising the peptide nucleic acid derivative according to claim 1, or a pharmaceutically acceptable salt thereof.

5. A cosmetic composition for improving skin aging by down-regulating human ACC2 gene expression, comprising the peptide nucleic acid derivative according to claim 1, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 11,739,124 B2 |
| APPLICATION NO. | : 17/266763 |
| DATED | : August 29, 2023 |
| INVENTOR(S) | : Han et al. |

It is certified that error appears in the above-identified patent and that said Letters Patent is hereby corrected as shown below:

In the Claims

Column 36 Line 34: Claim 1, Delete "-$(CH_2)$r-," and insert -- -$(CH_2)_7$-, --

Signed and Sealed this
Tenth Day of October, 2023

Katherine Kelly Vidal
*Director of the United States Patent and Trademark Office*